US011029226B2

(12) United States Patent
Davis et al.

(10) Patent No.: US 11,029,226 B2
(45) Date of Patent: *Jun. 8, 2021

(54) BODY MOUNTED MONITORING SYSTEM AND METHOD

(71) Applicants: Reebok International Limited, London (GB); Medidata Solutions, Inc., New York, NY (US)

(72) Inventors: Paul M. Davis, Blackstone, MA (US); William Marvin, Canton, MA (US); Steven Fastert, Chelmsford, MA (US); Kevin Dowling, Westford, MA (US); Paul E. Litchfield, Westborough, MA (US); Benjamin Schlatka, Lexington, MA (US); Gilman Callsen, Charlottesville, VA (US); Robert Rich, Westwood, MA (US); Dustin G. Simone, Westerly, RI (US); Keith A. Stern, Quincy, MA (US); Dennis Gaboriault, Millbury, MA (US)

(73) Assignees: Reebok International Limited, London (GB); Medidata Solutions, Inc., New York, NY (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/033,553

(22) Filed: Jul. 12, 2018

(65) Prior Publication Data

US 2018/0321097 A1 Nov. 8, 2018

Related U.S. Application Data

(63) Continuation of application No. 13/662,009, filed on Oct. 26, 2012, now Pat. No. 10,024,743.

(Continued)

(51) Int. Cl.
*G01L 5/00* (2006.01)
*G01M 7/08* (2006.01)
(Continued)

(52) U.S. Cl.
CPC ............ *G01L 5/0052* (2013.01); *A42B 3/046* (2013.01); *A61B 5/11* (2013.01); *A61B 5/6803* (2013.01);
(Continued)

(58) Field of Classification Search
CPC ......... A42B 3/046; A61B 5/11; A61B 5/6803; A61B 5/6814; A61B 2562/0219;
(Continued)

(56) References Cited

U.S. PATENT DOCUMENTS 7,693,668 B2 * 4/2010 Vock ........................ G01C 9/00
702/44
8,860,570 B2 10/2014 Thomas et al.
(Continued)

OTHER PUBLICATIONS

Kevin Mitchell, "Blades Get High-Tech Headgear," *The StarPhoenix*, Aug. 26, 2011, 2 pages.
(Continued)

*Primary Examiner* — Stephanie E Bloss
(74) *Attorney, Agent, or Firm* — Sterne, Kessler, Goldstein & Fox P.L.L.C.

(57) ABSTRACT

Apparatus, systems, and methods for monitoring head acceleration and/or forces acting thereon are disclosed. A device for monitoring an acceleration or a force acting on the head of a user includes a flexible article adapted to be worn on the head of the user; and a monitoring assembly coupled to the flexible article. The monitoring assembly includes a sensor for measuring a force on the head and transmitting data relating to the force, the sensor disposed proximate to the head, a processor adapted to receive the force data from the
(Continued)

sensor, and a flexible strip operatively connecting the sensor and the processor.

20 Claims, 23 Drawing Sheets

Related U.S. Application Data

(60) Provisional application No. 61/552,252, filed on Oct. 27, 2011.

(51) Int. Cl.
    *G01P 1/02*           (2006.01)
    *G01P 15/08*         (2006.01)
    *A42B 3/04*          (2006.01)
    *A61B 5/11*           (2006.01)
    *A61B 5/00*           (2006.01)

(52) U.S. Cl.
    CPC ............. *A61B 5/6814* (2013.01); *G01M 7/08* (2013.01); *G01P 1/023* (2013.01); *G01P 15/08* (2013.01); *A61B 2562/0219* (2013.01); *A61B 2562/0257* (2013.01)

(58) Field of Classification Search
    CPC ........ G01P 15/08; G01P 1/023; G01L 5/0052; G01M 7/08
    See application file for complete search history.

(56) References Cited

U.S. PATENT DOCUMENTS

| | | | |
|---|---|---|---|
| 10,024,743 B2 * | 7/2018 | Davis | ..................... A42B 3/046 |
| 2003/0163287 A1 | 8/2003 | Vock et al. | |
| 2005/0177929 A1 * | 8/2005 | Greenwald | ............... A61B 5/11 2/425 |
| 2007/0089480 A1 | 4/2007 | Beck | |
| 2009/0307827 A1 | 12/2009 | Aspray | |
| 2010/0180701 A1 | 7/2010 | Daniel et al. | |
| 2011/0181419 A1 * | 7/2011 | Mack | ........................ G01L 1/26 340/573.1 |
| 2011/0210685 A1 | 9/2011 | Liao | |
| 2011/0215931 A1 | 9/2011 | Callsen et al. | |
| 2011/0218756 A1 | 9/2011 | Callsen et al. | |
| 2011/0218757 A1 * | 9/2011 | Callsen | ..................... F41H 1/04 702/141 |
| 2011/0219852 A1 * | 9/2011 | Kasten | .................. G01L 5/0052 73/12.04 |
| 2013/0074248 A1 | 3/2013 | Evans et al. | |

OTHER PUBLICATIONS

"Impact Indicator™", Battle Sports Science™, 2 pages.
David Epstein, "Taking It on the Chin," *SI Vault*, CNN/Sports Illustrated, Jan. 31, 2011, 2 pages.
Press Release, "Battle Sports Science Launches the New, Revolutionary Impact Indicator," Battle Sports Science, Aug. 18, 2011, 2 pages.
Press Release, "THSCA Notebook," www.dallasnews.com, Jul. 27, 2011, 1 page.
Laird et al., "Chin Strap Signals Serious Impact," Battle Sports Science, *USA Today*, 1 page.
Eiband Martin, "Human Tolerance to Rapidly Applied Accelerations: A Summary of the Literature," Jun. 1, 1959, Nasa Technical Reports, NASA-MEMO-5-19-59E, E-345.

* cited by examiner

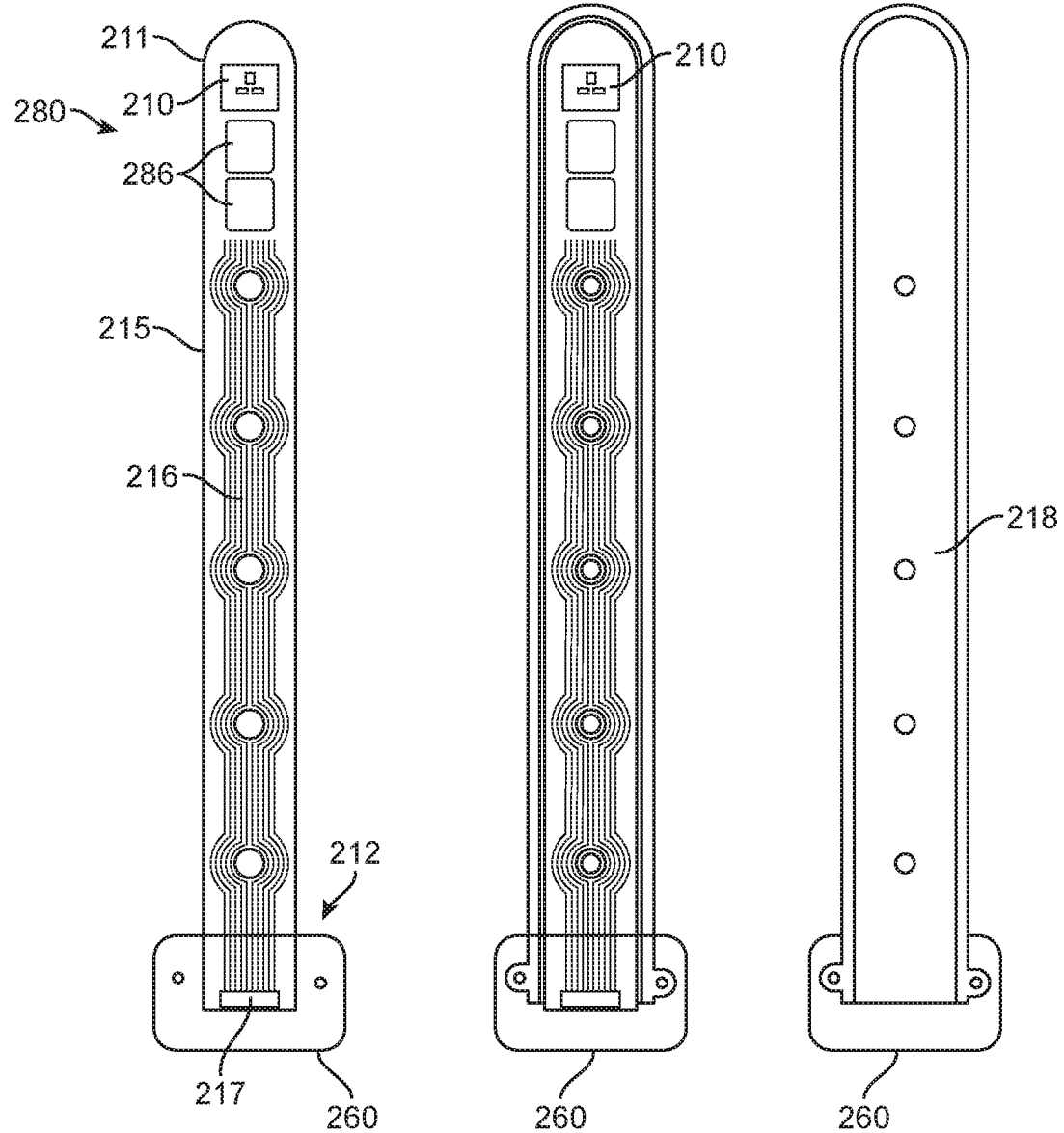

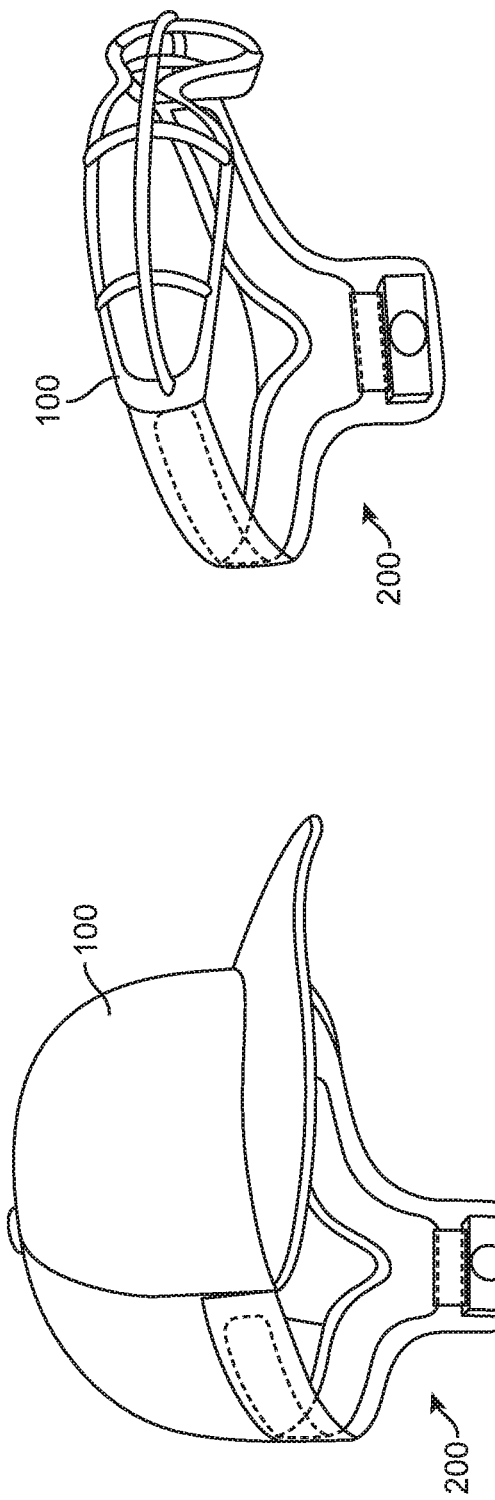
FIG. 11
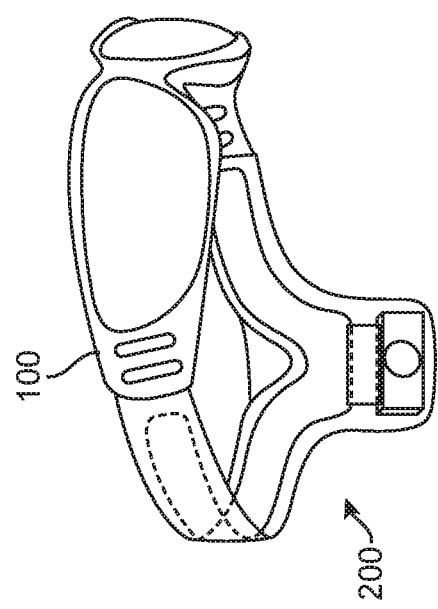
FIG. 12
FIG. 13

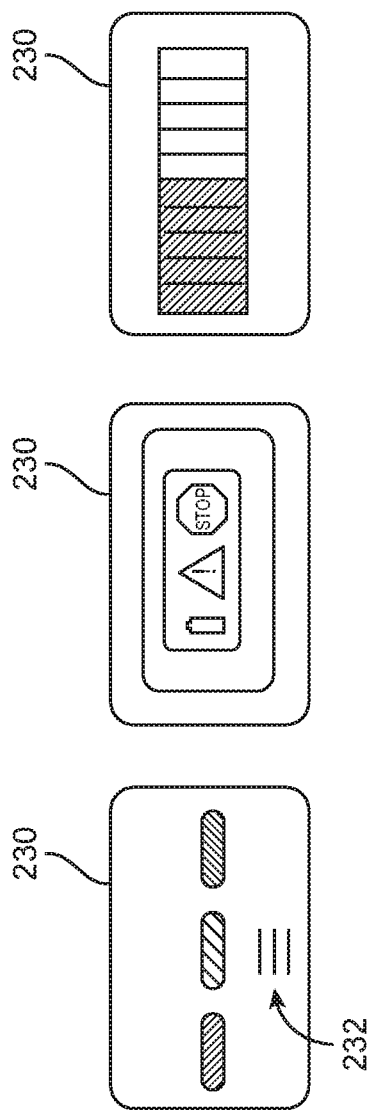

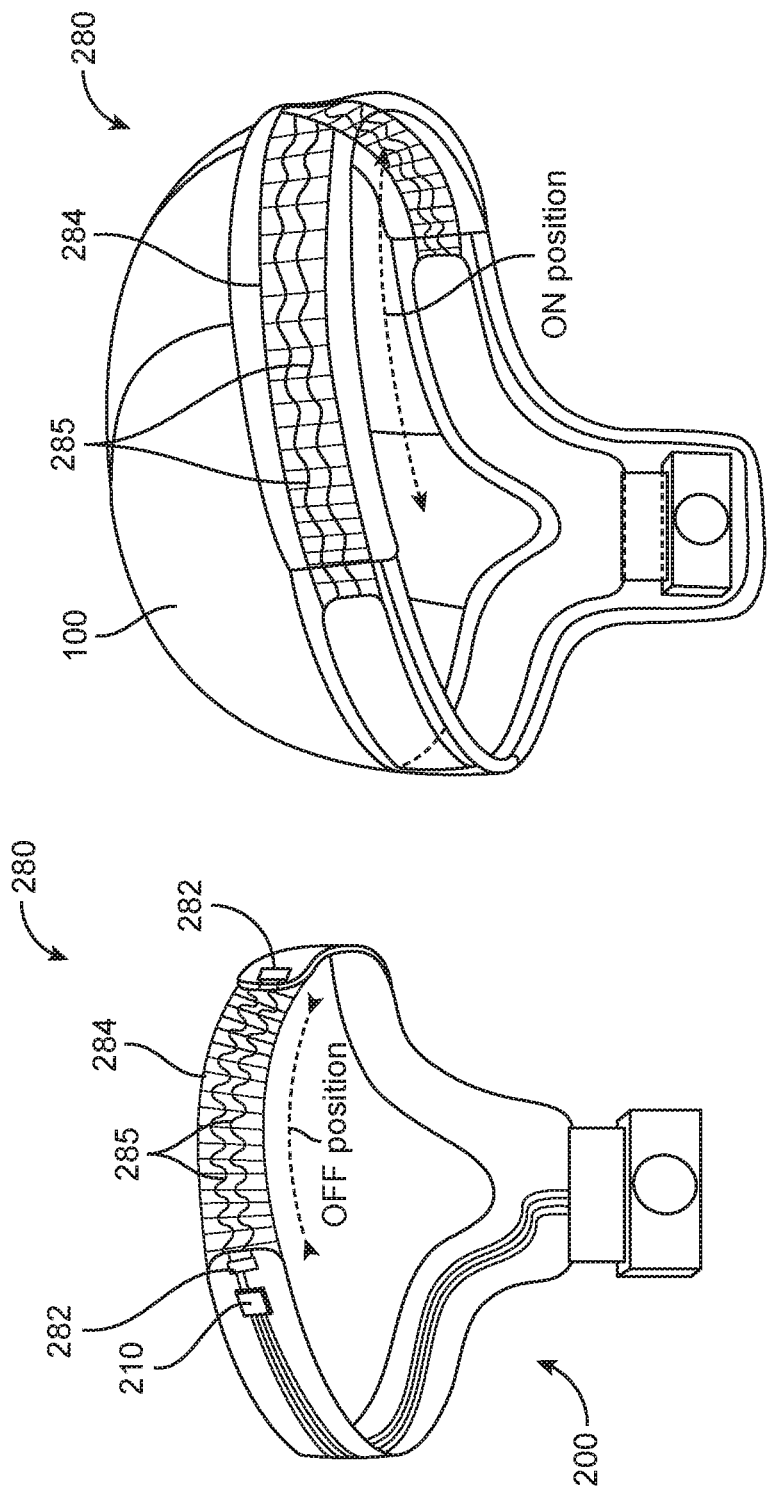

BODY MOUNTED MONITORING SYSTEM AND METHOD

CROSS-REFERENCE TO RELATED APPLICATION

This application is a continuation of U.S. patent application Ser. No. 13/662,009, filed Oct. 26, 2012 and entitled, "Body Mounted Monitoring System And Method," the disclosure of which is incorporated herein in its entirety by reference thereto. U.S. patent application Ser. No. 13/662,009 claims the priority of U.S. Provisional Application No. 61/552,252, filed Oct. 27, 2011, the disclosure of which is incorporated herein in its entirety by reference thereto.

BACKGROUND OF THE INVENTION

Field of the Invention

The present invention is directed to an apparatus, system, and method for monitoring accelerations of the head and corresponding forces acting thereon, including direct impact and indirect forces.

Background Art

In athletic endeavors as well as routine daily life, the frequency and diagnosis of head injuries has increased. These injuries may occur due to direct impact forces, such as those occurring in head-to-head, head-to-body, head-to-equipment, and head-to-ground impacts, and indirect forces such as those that may occur due to a snap or twist of the head or neck and/or due to an impact force to the body. In an effort to reduce these injuries and their complications or prevent further damage once an injury has occurred, systems and methods have been developed for monitoring impacts.

Many of these systems are used in athletic applications and include sensors that are permanently integrated into a protective helmet. As a result, the sensors are not positioned immediately proximate the head or in contact with the head, and may actually measure the acceleration of the helmet or to the chin or jaw, as opposed to the major part of the head. This may lead to less accurate measurements of forces to the head, and, thus, less effective monitoring of impact severity. Additionally, because some systems are permanently integrated with the helmet, they cannot be used separately from the helmet. Therefore, a continuing need exists for innovations in monitoring accelerations of the head and corresponding forces acting thereon, including direct impact and indirect forces.

BRIEF SUMMARY OF THE INVENTION

Embodiments of the present invention relate to a device for monitoring a force acting on the head of a user. In an embodiment, the device includes a flexible article adapted to be worn on the head of the user; and a monitoring assembly coupled to the flexible article. The monitoring assembly includes a sensor for measuring a force on the head and signaling or transmitting data relating to the force, the sensor positioned to be disposed immediately proximate to the head, a processor adapted to receive the force data from the sensor, and a flexible strip operatively connecting the sensor and the processor. In one embodiment, the flexible article may be an article of clothing, such as, a hat. The article may be flexible and stretchable, and may be conformable to the head, or a portion of the head, of the wearer. In one embodiment, the flexible article is adapted to conform to at least one portion of the user's head proximate to a region selected from the group consisting of: the cranium, the frontal bone, the temporal bone, the parietal bone, the sphenoid bone, the occipital bone, the scalp, and combinations thereof. In one embodiment, the sensor may comprise one or more than one accelerometer. In some embodiments, the accelerometer may be a low-g accelerometer.

In another embodiment, a device for monitoring acceleration of the head of a user includes a flexible article of clothing having first and second flexible layers conformable to the head of the user. The device may further include a sensor disposed between the first and second flexible layers for measuring an acceleration of the head and signaling or transmitting data relating to the acceleration; a control unit having a housing and a processor disposed in the housing for receiving the acceleration data from the sensor; and a flexible strip operatively connecting the sensor to the control unit. The control unit may be detachable from the flexible article of clothing. The flexible strip may include a first portion and a second portion more flexible than the first portion, and the control unit may be coupled to the more flexible portion. The flexible strip may include a first extension adapted to be positioned about a first side of the wearer's head and a second extension adapted to be positioned about a second side of the head. In one embodiment, the control unit may be disposed at the intersection of the first and second extension. In one embodiment, the device further includes a display for providing information related to the acceleration data to the user. The information may include visual, audible, and/or other indications related to the acceleration data. For example, the information may include an alert that the force(s) acting on the head of the user have exceeded a threshold. In one embodiment, the flexible article may include a pocket, and one or more of the sensor, the control unit, and the flexible strip may be disposed in the pocket.

In another embodiment, a method of monitoring forces on the head of a user includes providing a wearable monitor conformable to the head of the user having at least one accelerometer and at least one gyroscope to be positioned proximate to the head of a user; collecting data from the at least one accelerometer and the at least one gyroscope about an acceleration of the head; and conveying information related to the acceleration to the user. The at least one accelerometer and at least one gyroscope may be positioned proximate to at least one of the cranium, the frontal bone, the temporal bone, the parietal bone, the sphenoid bone, the occipital bone, and/or the scalp.

Another embodiment includes a method of monitoring acceleration of the head and corresponding forces acting thereon. The method includes determining a translational acceleration of the head using a low-g sensor adapted to be positioned immediately proximate the head; determining the orientation of the sensor with respect to gravity; modifying the translational acceleration based on the orientation determination; comparing the modified translational acceleration and a predetermined threshold acceleration level; and conveying information to the user based on the comparison. The threshold acceleration level may be a reference characteristic indicative of an impact severity.

Another embodiment includes a modular head impact monitoring system. In one embodiment, the system includes a rigid helmet for protecting the head of a wearer; a conformal headpiece including an outer conformal layer formable to the head of the user and adapted to be worn intermediate the rigid helmet and the head; and a sensor unit coupled to the headpiece and adapted to be disposed intermediate to the head and the outer conformal layer for measuring an acceleration of the head, and wherein the headpiece is adapted to be worn separately from the helmet. The rigid helmet may be a sports helmet, an industrial helmet, a military helmet, or the like.

Yet another embodiment includes a device for monitoring a force acting on a head of a user. The device includes a flexible article adapted to be worn on the head of the user; and a monitoring assembly coupled to the flexible article. The monitoring assembly includes: a sensor for measuring a force on the head and transmitting data relating to the force, the sensor positioned to be disposed proximate to the cranium and comprising at least one low-g accelerometer adapted to measure accelerations of no more than about 24 g, and a processor adapted to receive the force data from the sensor. The sensor may be positioned to be disposed proximate to the temporal bone or the parietal bone of the head, for example.

Some embodiments of the present invention may include one or more features disclosed in U.S. Patent Pub. No. 2011/0218757 to Callsen et al., entitled "Methods and Apparatus Having Power Control Features for Conformal Sensing of Change in Motion of a Body Part," published Sep. 8, 2011, U.S. Patent Pub. No. 2011/0218756 to Callsen et al., entitled "Methods and Apparatus for Conformal Sensing of Force and/or Acceleration at a Person's Head," published Sep. 8, 2011, and U.S. Patent Pub. No. 2011/0215931 to Callsen et al., entitled "Methods and Apparatus for Assessing Head Trauma Based on Conformal Sensing of Force and/or Change in Motion of a Person's Head," published Sep. 8, 2011, the disclosures of which are hereby incorporated in their entirety by reference thereto.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

FIG. 7A is a plan view of a flexible strip including a sensor according to an embodiment of the present invention.

FIG. 7B is a plan view of a partially encapsulated flexible strip of FIG. 7A according to an embodiment of the present invention.

FIG. 7C is a plan view of an encapsulated flexible strip according to an embodiment of the present invention.

FIG. 11 is a schematic illustration of a monitoring system according to an embodiment of the present invention.

FIG. 12 is a schematic illustration of a monitoring system according to an embodiment of the present invention.

FIG. 13 is a schematic illustration of a monitoring system according to an embodiment of the present invention.

FIG. 18 is a schematic illustration of a display according to an embodiment of the present invention.

FIG. 19 is a schematic illustration of a display according to an embodiment of the present invention.

FIG. 20 is a schematic illustration of a display according to an embodiment of the present invention.

FIG. 22 is a schematic illustration of a power management system in an OFF position according to an embodiment of the present invention.

FIG. 23 is a schematic illustration of a power management system in an ON position according to an embodiment of the present invention.

DETAILED DESCRIPTION OF THE INVENTION

Figure 1:
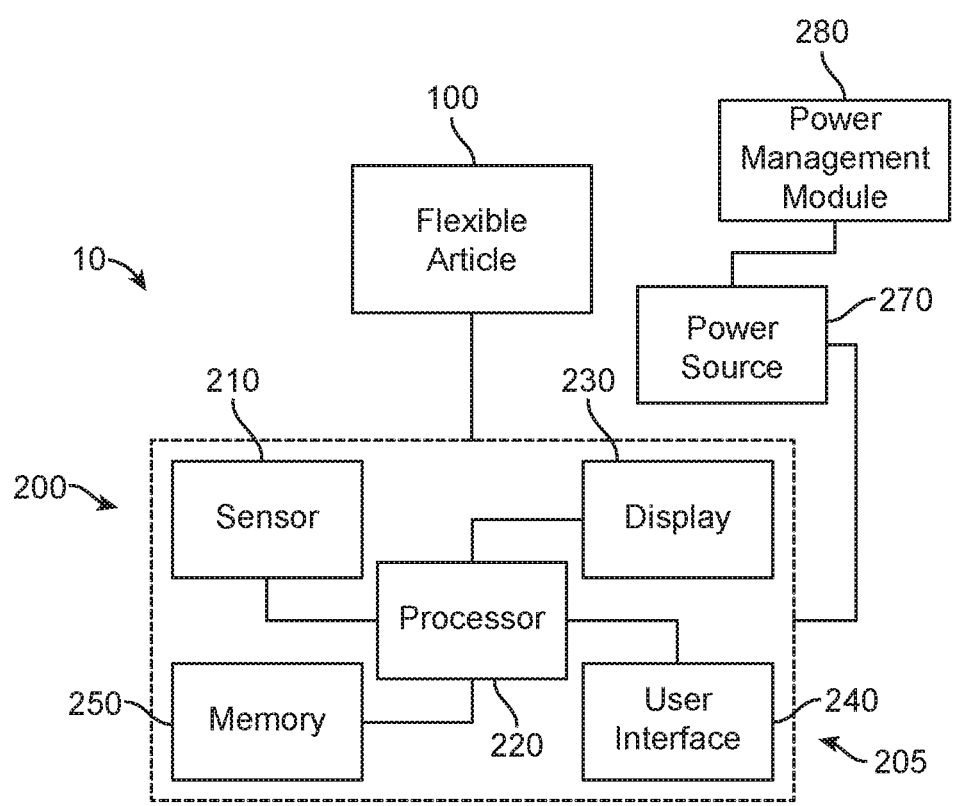
FIG. 1 is a block diagram of a monitoring system according to an embodiment of the present invention.

The present invention will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present invention. Other suitable modifications and adaptations of the variety of conditions and parameters normally encountered in the field, and which would be apparent to those skilled in the art, are within the spirit and scope of the invention.

Embodiments of the present invention include a system 10 for monitoring accelerations and/or corresponding forces acting on a head, or a portion of a head, of a user. In various embodiments, the present invention includes a system 10 for monitoring accelerations and/or corresponding forces acting on at least one portion of the head of a user selected from the group consisting of the skull, the cranium, the frontal bone, the temporal bone, the parietal bone, the sphenoid bone, the occipital bone, or the scalp of the user, or a combination thereof. For example, in one particular embodiment, the present invention includes a system 10 for monitoring accelerations and/or corresponding forces acting on the cranium or at least one of the temporal bone and the parietal bone. The system 10 includes a flexible article 100 adapted to be worn on the head of the user and a monitoring assembly 200 coupled to the flexible article for measuring an acceleration of at least a portion of the head and/or a corresponding force acting thereon.

The monitoring assembly 200 includes at least one sensor 210 for measuring an acceleration of the head (or a portion of a head such as those selected from the group consisting of the skull, the cranium, the frontal bone, the temporal bone, the parietal bone, the sphenoid bone, the occipital bone, or the scalp of the user, or a combination thereof) and may use information relating to this acceleration to provide information or alerts to the user. For example, the monitoring assembly 200 may provide an indication to the user that a certain level of acceleration or force (one-time or cumulative) has acted on the head or portion of the head of the wearer. Because in certain embodiments the sensor 210 is provided immediately proximate to, or in contact with, the head or a portion of the head, the monitoring assembly 200 may provide accurate data regarding the acceleration undergone by the head, and, thus, the force or forces acting on the head. These forces may derive from direct impact forces acting on the head, such as, for example, head-to-head, head-to-body, head-to-equipment, head-to-structure, and head-to-ground impacts, and/or indirect impact forces that may occur due to a twist or snap of the neck or head and/or due to an impact force to the body. Moreover, these forces may occur during an athletic activity, work activity, routine daily activity or at any time. Because the effects of an acceleration of the head—and the corresponding force acting on the head—may lead to injury, system 10 provides a useful tool for monitoring, alerting, and/or possibly reducing or preventing injury to athletes, workers, children, and other users.

In some embodiments, the term "user" as used herein may include the wearer of all or a portion of the monitoring system 10 and/or an individual (e.g., coach, trainer, supervisor, or parent) who may not be wearing any portion the monitoring system 10 but who may be monitoring the data provided by the system.

Figure 2:
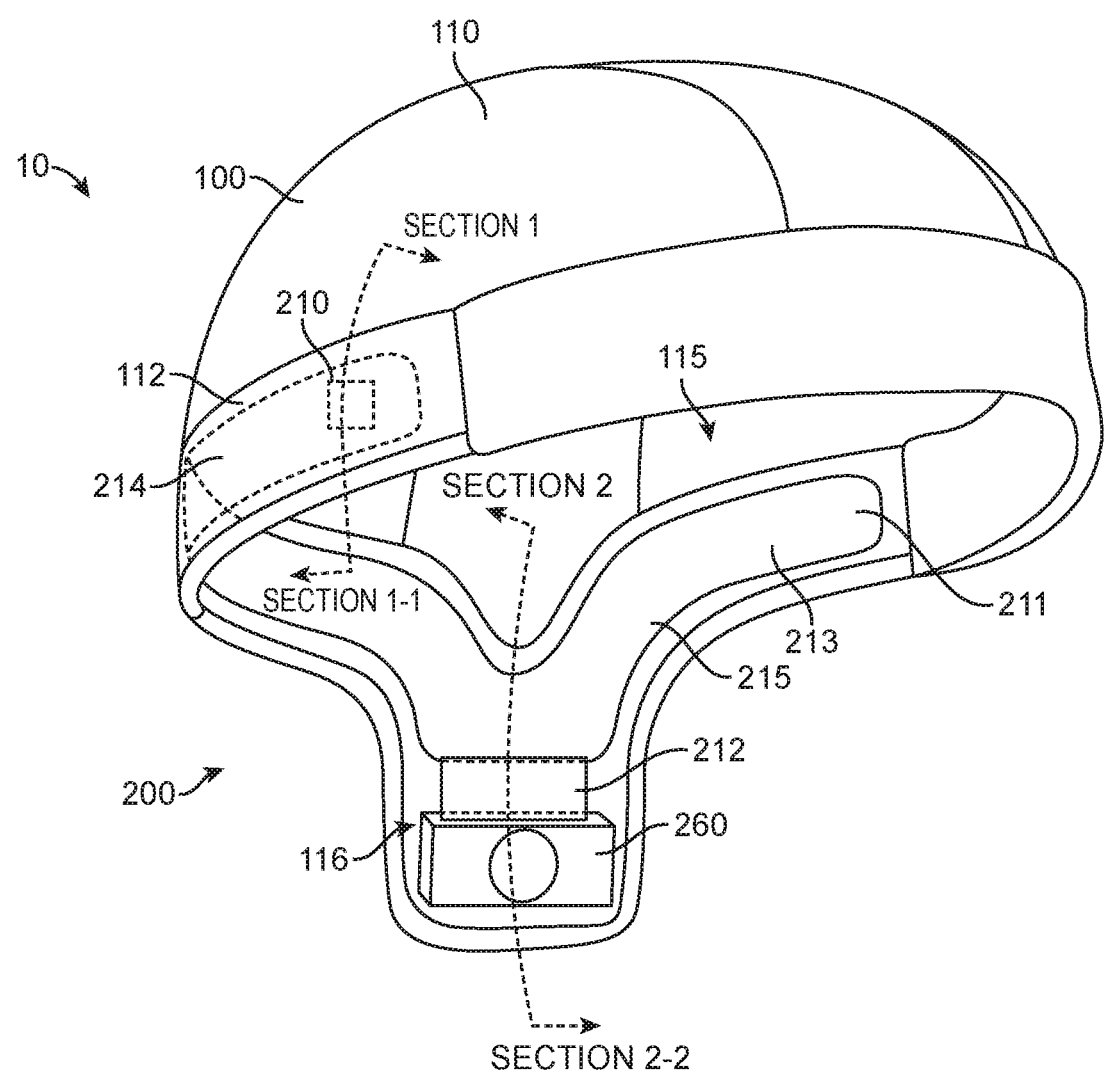
FIG. 2 is a schematic illustration of a head monitoring system according to an embodiment of the present invention.

With reference to FIGS. 1 and 2, in one embodiment the monitoring assembly 200 further includes a processor 220 adapted to receive data from the sensor 210 and a flexible strip 215 operatively connecting the sensor 210 and the processor 220. The monitoring assembly 200 may include a control unit 205 which includes processor 220 and may further include a display 230, a user interface 240, and a memory 250, such as, for example, flash memory for storing data received from sensor 210. The user interface 240 may allow the user to input information, such as personalized settings, into the monitoring assembly 200. In some embodiments, monitoring assembly 200 may be adapted to connect to a remote computer via a wireless or wired connection to allow the user to input, review, manipulate, and report data. The remote computer may include a desktop computer, a laptop computer, a tablet computer, a smartphone, or other suitable computing device. In one embodiment, one or more components of the monitoring assembly 200 may be disposed within a housing 260. The monitoring assembly 200 may further include a power source 270 operatively connected to one or more of the assembly components for providing power thereto. In one embodiment, the power source 270 may be disposed within housing 260. In some embodiments, at least some of the components of monitoring assembly 200 are physically connected by an electrical connection. In other embodiments, one or more of the components of monitoring assembly 200 are wirelessly connected. For example, in one embodiment display 230 and/or user interface 240 are wirelessly connected to at least one of the other components of monitoring assembly 200. In another example embodiment, sensor 210 is wirelessly connected to at least one of the other components of monitoring assembly 200.

Processor 220 is operatively connected to sensor 210 and is adapted to receive the measured data from the sensor. As discussed in more detail below, the data received by the processor 220 is processed using computer readable logic stored in monitoring assembly 200 (e.g., on processor 220) to assess the level of acceleration and/or corresponding force acting on the head, or on a portion of the head, and to determine whether an alert needs to be provided to the user based on the acceleration and/or force level assessment. In one embodiment, the assessment may include a comparison of the measured data, or a parameter value based on the measured data, to a threshold value. If the measured data or parameter value exceeds the threshold value, processor 220 may send a signal to display 230 and display 230 may provide a corresponding visual and/or audible indication to the user. In one embodiment, sensor 210 sends raw acceleration data to processor 220. Processor 220 may then process the raw acceleration data and calculate modified acceleration data and corresponding force data. In other embodiments, sensor 210 may include sufficient processing capability to manipulate raw acceleration data and provide modified acceleration data and/or corresponding force data to the processor 220.

With reference to FIGS. 1-4, in some embodiments the system 10 comprises a flexible article of clothing 100. In one embodiment, the flexible article 100 is flexible such that it may be adapted to be worn on the head of the wearer. For example, flexible article 100 can wrap about the head, e.g., the crown, sides, and/or back of the head, and take the form of the head or a portion of the head such as at least one of the crown, sides, and/or back of the head. In some embodiments, at least a portion of flexible article 100 is also stretchable such that such portion of flexible article 100 stretches about the crown, sides, and/or back of the head to take the form of the head or a portion of the head such as at least one of the crown, sides, and/or back of the head. In some such embodiments, at least a portion of flexible article 100 is stretchable so as to substantially conform to a variety of head shapes and sizes. For example, flexible article 100 can be stretchable so as to fit snugly about the head of a user when the flexible article is worn. In one embodiment, flexible article 100 may be both flexible and stretchable such that it is conformable to the head or a portion of the head such as, e.g., the crown, sides, and/or back of the head of the wearer. In preferred embodiments, when it is worn, flexible article 100 lies in close proximity to a portion of the head of a user selected from the group consisting of the skull, the cranium, the frontal bone, the temporal bone, the parietal bone, the sphenoid bone, the occipital bone, or the scalp of the user, or a combination thereof. For example, flexible article 100 can lie adjacent to the cranium region of the head or adjacent to at least one of the temporal bone region and the parietal bone region.

In exemplary embodiments, as shown in FIG. 2, flexible article 100 comprises a hat such as, for example, a beanie, a skull cap, or a do-rag. The hat 100 may comprise a crown portion 110, a side portion, and/or a back portion adapted to conform to the crown, the sides, and/or the back of the head of the wearer. The crown portion 110 is coupled to a base portion 112 which extends radially about all or a portion of the head of the user below the crown. In one embodiment, base portion 112 covers the front, rear, and temple areas of the head. The base portion 112 may include an inner layer 111, an outer layer 113, and a binding region 114 wherein the inner and outer layers are connected. In some embodiments, binding region 114 comprises a binding material such as, for example, stitching, adhesive, or polymer layer. In other embodiments, binding region comprises the inner layer and outer layer joined by welding, heat sealing, or another method of connecting the inner and outer layers.

The hat 100, including the crown portion 110 and/or the base portion 112, is preferably made of a material having suitable flexibility and stretchability. All or a portion of the hat 100 is also preferably made from a material that is breathable to provide comfort to the wearer and water-resistant, absorbent, or wicking to provide perspiration management. Suitable materials include woven, non-woven, and knitted (e.g., flat or circular knitted) fabrics. In some embodiments, crown portion 110 may be made of a perforated fabric or a mesh material such as, for example, jersey mesh. Other man-made and natural materials can also be used for crown portion 110 including, but not limited to, spandex, neoprene, nylon, polyester, polypropylene, cotton, wool, and combinations thereof. In one embodiment, base portion 112 including one or both of the inner and outer layers may be made of neoprene. Other man-made and natural materials can also be used for base portion 112 including, but not limited to, spandex, neoprene, nylon, polyester, polypropylene, cotton, wool, and combinations thereof. The crown portion 110 and the base portion 112 may be coupled by stitching, adhesive, welding, heat sealing, or other suitable means. In one embodiment, hat 100, including crown portion 110 and base portion 112, may be unitary and formed from a single fabric. In some embodiments, hat 100 may include a high friction or textured material to help hold the hat to the wearer's body. For example, hat 100 may include a region of printed silicon such as a band of printed silicon.

Figure 3:
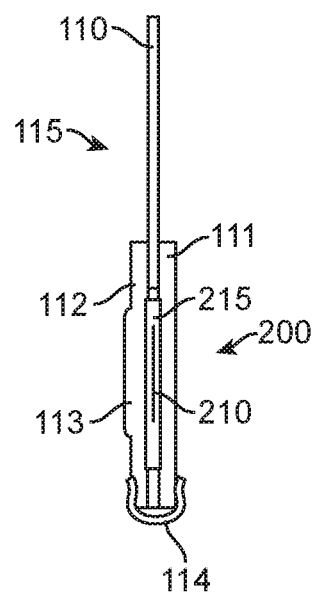
FIG. 3 is a cross-sectional view of a portion of monitoring assembly along the section lines 1-1 of FIG. 2 according to an embodiment of the present invention.
Figure 5:
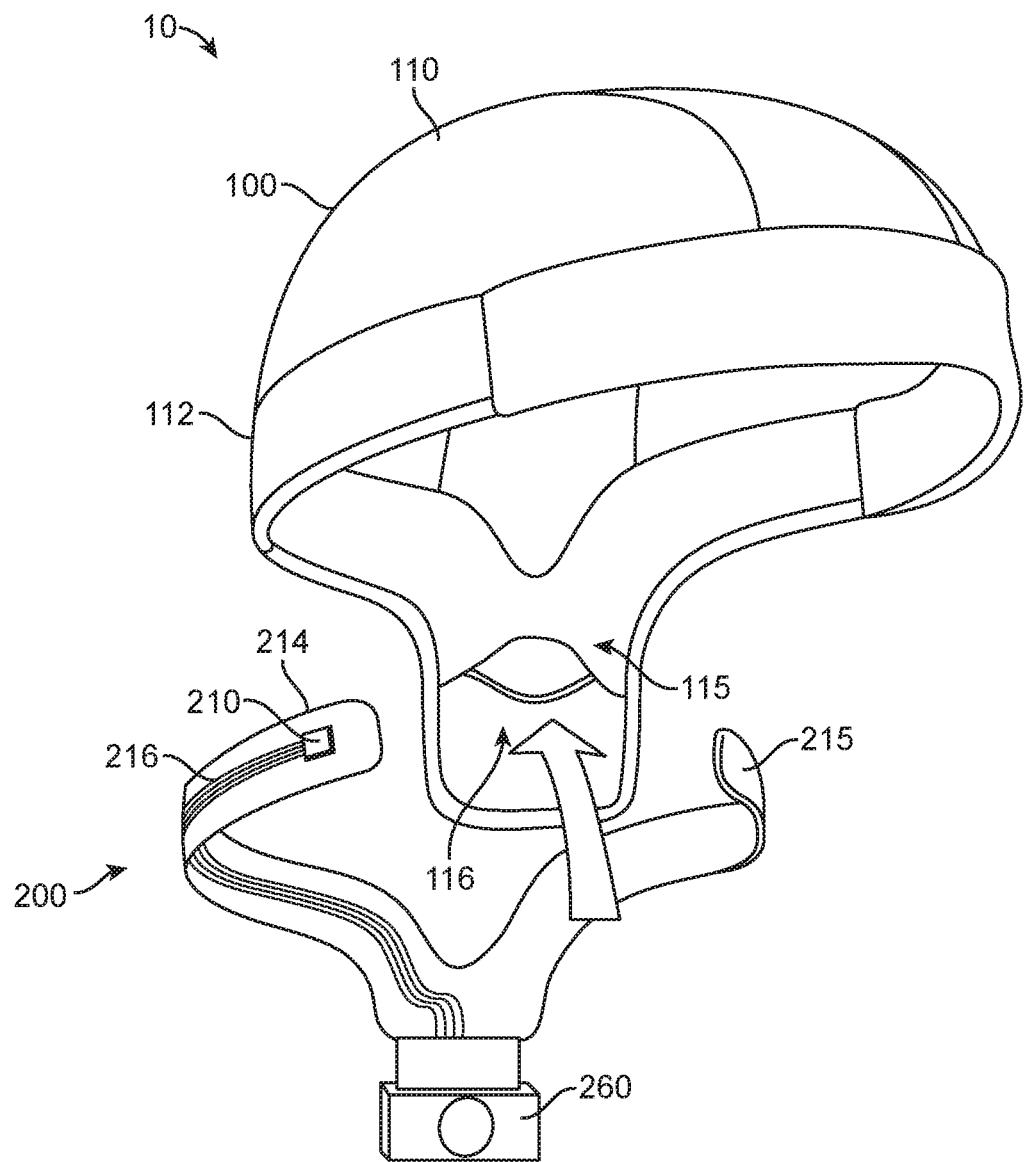
FIG. 5 is a schematic illustration of a monitoring assembly removably attached to a headpiece according to an embodiment of the present invention.

In one embodiment, flexible article 100 such as hat 100 may include a pocket 115 for receiving all or a portion of the monitoring assembly 200. As shown in FIGS. 2, 3, and 5, for example, in one embodiment pocket 115 may receive the flexible strip 215 and the housing 260 including processor 220. In one embodiment, the inner layer 111 and outer layer 113 of the hat 100 may define the pocket 115. In this manner, the pocket 115 facilitates placement of sensor 210 immediately proximate to the head, or a portion of the head, of the wearer. In preferred embodiments, when the system 10 is worn, sensor 210 lies in close proximity to a portion of the head of a user selected from the group consisting of the skull, the cranium, the frontal bone, the temporal bone, the parietal bone, the sphenoid bone, the occipital bone, or the scalp of the user, or a combination thereof. For example, sensor 210 can lie adjacent to the cranium region of the head or adjacent to at least one of the temporal bone region and the parietal bone region. In a specific embodiment, sensor 210 can lie adjacent to the temporal bone region of the head. In additional preferred embodiments, only the inner layer 111 of the flexible article 100 defining the pocket separates the monitoring assembly 200 in the vicinity of sensor 210 from a head surface of the user. For example, only the inner layer 111 of a hat 100 defining the pocket separates the monitoring assembly 200 in the vicinity of sensor 210 from a portion of the head of a user in the vicinity of the skull, the cranium, the frontal bone, the temporal bone, the parietal bone, the sphenoid bone, the occipital bone, or the scalp, or a combination thereof. In one specific embodiment, only the inner layer 111 of a hat 100 defining the pocket separates the portion of the monitoring assembly 200 overlying sensor 210 from a portion of the head of a user in the cranium region or in at least one of the temporal bone region and the parietal bone region. It is thought that by positioning sensor 210 in this manner, i.e., close to the skull, the cranium, the frontal bone, the temporal bone, the parietal bone, the sphenoid bone, the occipital bone, or the scalp of the user, more accurate determinations of acceleration and/or direct and indirect forces of the head can be made as compared to when known devices are used.

Figure 4:
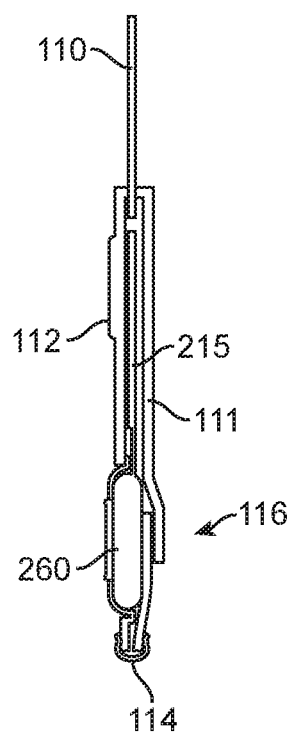
FIG. 4 is a cross-sectional view of a portion of monitoring assembly along the section lines 2-2 of FIG. 2 according to an embodiment of the present invention.

In one embodiment, as shown in FIGS. 4 and 5, pocket 115 may include an opening 116 to facilitate placement of the monitoring assembly 200 within the pocket. The opening 116 may include an opening in the inner layer 111. In one embodiment, the inner layer 111 comprises a thin layer of material so as to allow placement of the sensor 210 immediately proximate to the head or to a portion of the head.

The monitoring assembly 200 may be removably coupled to the flexible article 100. In some embodiments, this may facilitate washing the flexible article 100 after use, and may also facilitate modularity of the monitoring system 10, as discussed below. The pocket 115 may also help to support monitoring assembly 200 and to maintain proper positioning of the monitoring assembly 200 about the head of the wearer. In some embodiments, monitoring assembly 200 may be integral with the flexible article 100 such that it is securely attached to the flexible article using stitching, adhesive, or other suitable means.

In one embodiment, sensor 210 comprises one or more accelerometers for measuring an acceleration of the head or a portion of the head. The sensor 210 is adapted to be worn immediately proximate to the head, and, in some embodiments, in contact with the head. As such, the measured acceleration may provide more accurate data regarding the acceleration undergone by the head and the force or forces acting on the head. In some embodiments, this configuration can provide more accurate and/or useful data as compared to systems which have sensors that are not positioned immediately proximate to the head such as, for example, proximate to the skull, the cranium, the frontal bone, the temporal bone, the parietal bone, the sphenoid bone, the occipital bone, or the scalp of the user. For example, such systems may include an accelerometer disposed within a rigid helmet that has substantial material thickness and prevents the accelerometer from being positioned immediately proximate to the head. In some systems, an accelerometer is disposed away from the skull, the cranium, the frontal bone, the temporal bone, the parietal bone, the sphenoid bone, the occipital bone, and the scalp on another portion of the head. In these systems, the accelerometer may only be capable of providing acceleration data of the helmet itself or another portion of the body, and cannot provide accurate or useful data related to acceleration of the wearer's head. This may result in a less accurate monitoring system.

In one embodiment, the sensor 210 comprises one or more multi-axis accelerometers adapted to measure the translational acceleration of the head in multiple directions. In one embodiment, the sensor 210 comprises a tri-axial accelerometer. In one embodiment, the sensor 210 may comprise a low-g accelerometer adapted to measure low translational acceleration of the head. In one embodiment, the low-g accelerometer can accurately measure accelerations of no more than about 50 g, such as no more than 40 g or no more than 30 g. In other embodiments, the low-g accelerometer can accurately measure accelerations of no more than about 24 g. In another embodiment, the low-g accelerometer can accurately measure accelerations of no more than about 20 g. In one embodiment, sensor 210 may comprise a Bosch Sensortec BMA 220 low-g triaxial accelerometer. Other suitable accelerometers, including, but not limited to, a Bosch BMA 250 accelerometer, a ST Microelectronics LIS331HH accelerometer, and an Analog Devices ADXL345 accelerometer, may be used.

Sensor 210 may be adapted to determine the relative orientation of the sensor axes with respect to gravity. In some embodiments, processor 220 may determine the relative orientation based upon data provided to it by sensor 210. The relative orientation information may be used to determine rotation of the head and may be used in determining a qualitative or quantitative measurement of the force acting on the wearer's head. In one embodiment, sensor 210 may include one or more gyroscopes to measure rotation of the head. For example, sensor 210 may include one or more single or multi-axis gyroscopes or a combination thereof. Suitable gyroscopes may include, but are not limited to, an ST Microelectronics L3G4200D gyroscope, a Bosch SMG060 gyroscope, an Analog Devices ADXRS150 gyroscope, and an InvenSense ITG-3200 gyroscope. In some embodiments, at least one gyroscope may be used in conjunction with at least one accelerometer to collect data about an acceleration of the head.

In some instances, monitoring assembly 200 can comprise at least one additional device to aid in determining or verifying the direction of an acceleration of the head. For example, monitoring assembly 200 can comprise at least one additional device selected from the group consisting of GPS receivers, wireless receivers, and inertial sensors (e.g., INS-type sensing devices).

Processor 220 and sensor 210 are operatively electrically connected by flexible strip 215. As shown in FIG. 2, in one embodiment flexible strip 215 includes a sensor end 211 at which the sensor 210 may be operatively connected and a processor end 212 at which the processor 220 may be operatively connected. In this manner, flexible strip 215 may include a flexible circuit. In one embodiment, as shown in FIGS. 6A-6C and 7A-7C, flexible strip 215 includes an electrical circuit 216 providing an operative electrical connection between the sensor 210 and the processor 220 and one or more electrical contacts 217 for operatively electrically connecting to the processor 220. All or a portion of the flexible strip 215 may be covered with an outer protective layer 218. In one embodiment, flexible strip 215 comprises one or more flexible, electrically conductive materials. The flexibility of flexible strip 215 facilitates placement of the sensor 220 immediately proximate to, or in contact with, the head, or a portion of the head, of the wearer.

Figure 8:
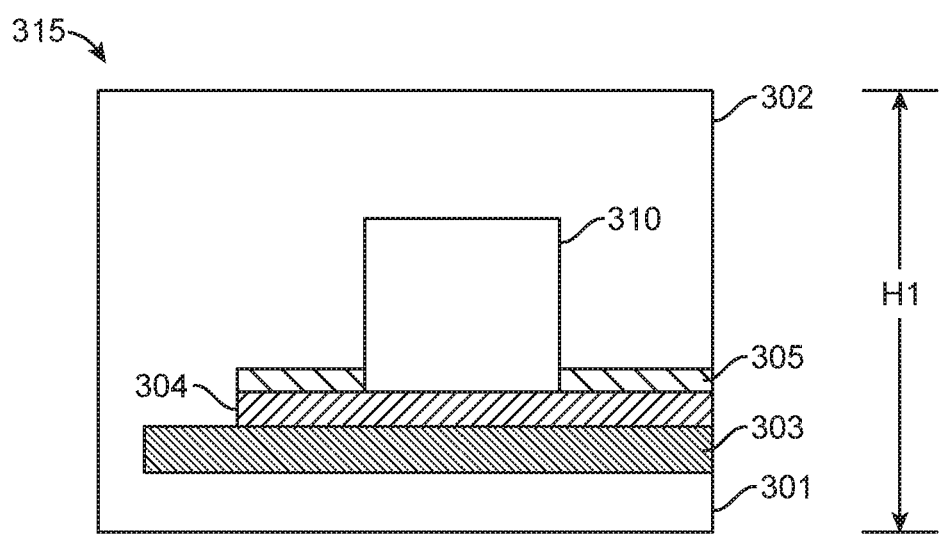
FIG. 8 is an exemplary schematic cross-section of a flexible strip according to an embodiment of the present invention.

With reference to FIG. 8, in which like reference numerals may refer to like elements, a flexible strip 315 according to an embodiment of the present invention will now be described. FIG. 8 is intended for illustrative purposes only and is not intended to be drawn to scale. In one embodiment, flexible strip 315 includes a copper layer 304 disposed on a polyimide base layer 303. A polyimide cover layer 305 is disposed on the copper layer 304, and a sensor 310 may be electrically connected through polyimide cover layer 305. A lower outer layer 301 and an upper outer layer 302 may comprise a thin encapsulation layer that may protect the electronic components of the flexible strip 315. Lower and upper outer layers may comprise any suitable encapsulation material, including, but not limited to, epoxy resin, polyurethane resin, plastic, silicone, or other suitable material. Copper layer 304 provides an electrical path between sensor 310 and other components of the monitoring assembly 200, including processor 220. The polyimide base layer 303 and the polyimide cover layer 305 may facilitate electrical conduction and may provide protection of the copper layer 304. In some embodiments, a portion of one or both of the polyimide layers can be cut away between conductors to enhance flexibility of flexible strip 315. Copper layer 304 may incorporate geometries that facilitate and enable flexing and stretching of the flexible strip 315 while maintaining a reliable electrical connection. For example, in some embodiments copper layer 304 may comprise a zig-zag or serpentine geometry. In some embodiments, flexible strip 315 may further include a conductive film (not shown), such as, for example, an Anisotropic Conductive Film (ACF), another suitable film, or solder to connect components (e.g., sensor 210) to a conductive path.

The materials and geometry of the flexible strip 315 enable a thin construction to be used. In one embodiment, the height H1 of flexible strip 315 may be less than about 2 mm. In some embodiments, the height of flexible strip 315 may be in the range of about 1 mm to about 2 mm. In other embodiments, the height of flexible strip 315 may be less than about 1 mm such as less than about 0.5 mm or less than 0.2 mm. In some instances, height H1 of flexible strip 315 can be in the range from about 50 microns to about 200 microns. The thin construction enhances the flexibility of flexible strip 315 and allows placement of the sensor 310 immediately proximate to, or in contact with, the head of the wearer. In some embodiments, sensor 310 can include unpackaged devices such as, for example, an unpackaged accelerometer and/or gyroscope. In some instances, sensor 310 can include die or thinned die devices or devices having planarization layers with interconnects.

In one embodiment, as shown in FIGS. 2 and 6A-6C, flexible strip 215 may have a generally Y-shaped configuration. In this embodiment, flexible strip 215 may include a first arm 214 adapted to be positioned about a first side of the wearer's head during use. For example, as shown in FIG. 2, first arm 214 may include sensor end 211 and first arm 214 may be configured such that sensor end 211 including sensor 210 is positioned in the temple area (e.g., in the region of the temporal bone) of the wearer during use. In one embodiment, flexible strip 215 may include a second arm 213 adapted to be positioned about a second side of the wearer's head during use. In some embodiments, the second arm 213 may include a sensor 210 disposed at an end thereof. In other embodiments, second arm 213 may act as a support arm to help maintain proper positioning of the monitoring assembly about the head of the wearer. In one embodiment, housing 260 may be disposed intermediate to the first arm 214 and the second arm 213, for example, at the intersection of the first and second arms. The flexibility and shape of flexible strip 215 facilitates placement of the sensor 220 immediately proximate to the head of the wearer.

Figure 9:
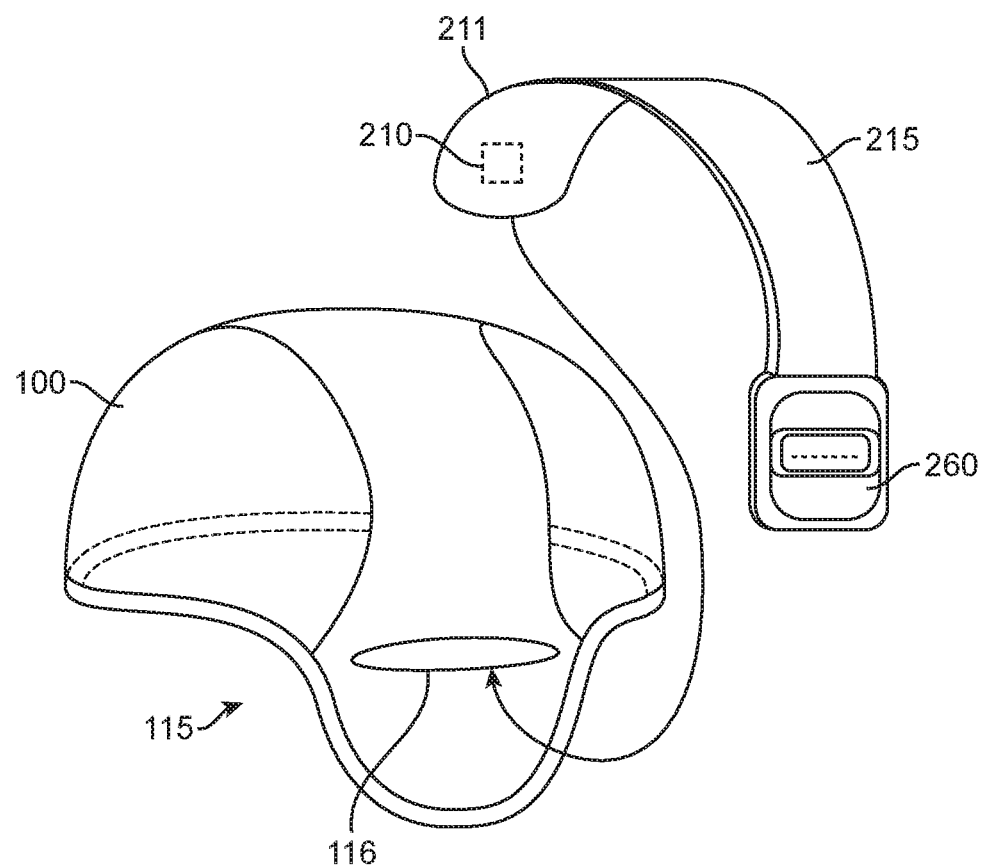
FIG. 9 is a schematic illustration of a monitoring assembly having a linear flexible strip according to an embodiment of the present invention.

In another embodiment, as shown in FIGS. 7A-7C, for example, flexible strip 215 may comprise a single linear strip having a sensor end 211 at which the sensor 210 may be operatively connected and a processor end 212 at which the processor 220 may be operatively connected. In one such embodiment, the flexible strip 215 may be configured such that sensor end 211 including sensor 210 is positioned proximate to the skull, the cranium, the frontal bone, the temporal bone, the parietal bone, the sphenoid bone, the occipital bone, and/or the scalp of the wearer during use. For example, as shown in FIG. 9, the sensor end 211 of the linear flexible strip 215 may be positioned in the front area of the head near the frontal bone or the forward portion of the parietal bone.

Figure 10:
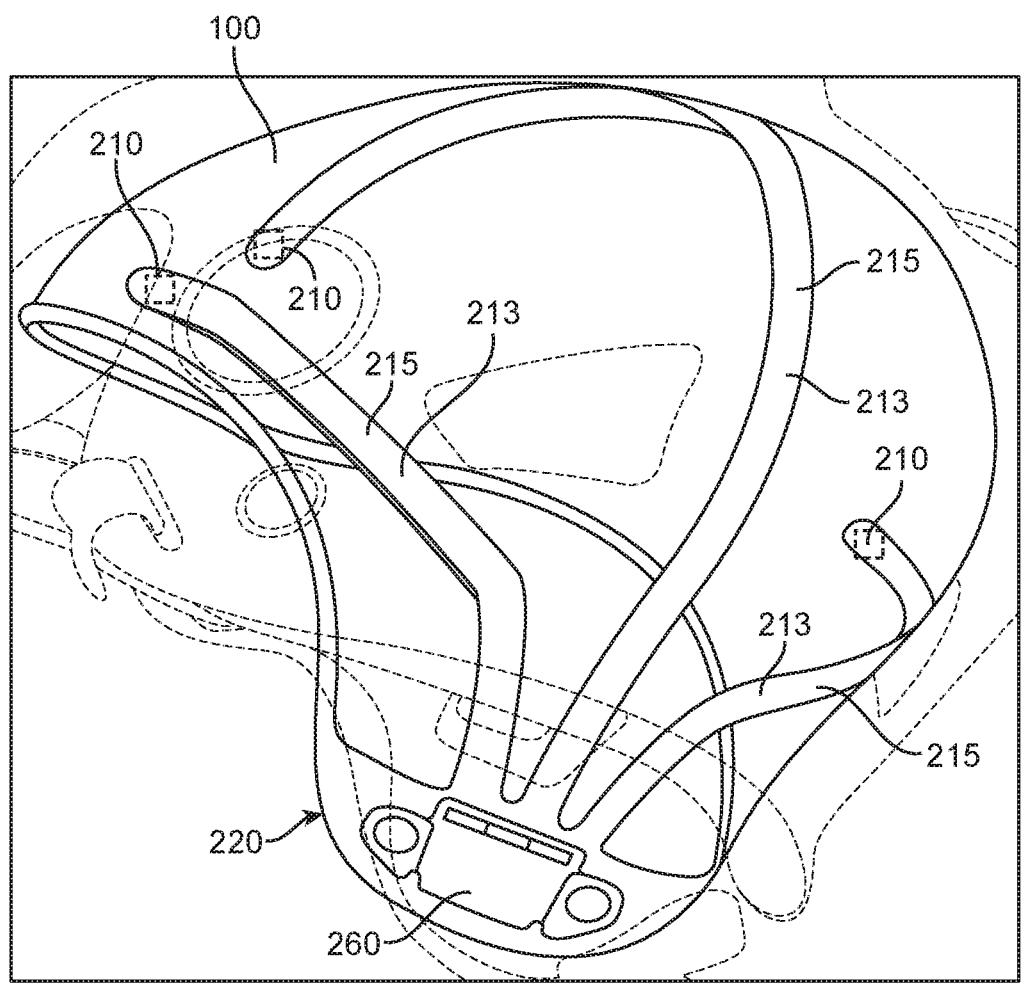
FIG. 10 is a schematic illustration of a monitoring assembly having a plurality of sensors according to an embodiment of the present invention.

Monitoring assembly 200 may be configured with a flexible strip 215 having one or more arms 213 which provide placement of one or more sensors 210 immediately proximate to the head of the user and/or which provide support to maintain the position of the sensors. For example, as shown in FIG. 10, flexible strip 215 may include three arms 213 each having a sensor 210 disposed at its end. In this embodiment, the flexible strip 215 may be configured such that sensor 210 is positioned in the front area, the rear area, and the temple area of the wearer during use. As will be appreciated, other configurations for providing placement of any number of sensors 210 about the wearer's head for monitoring may be utilized.

Figure 15:
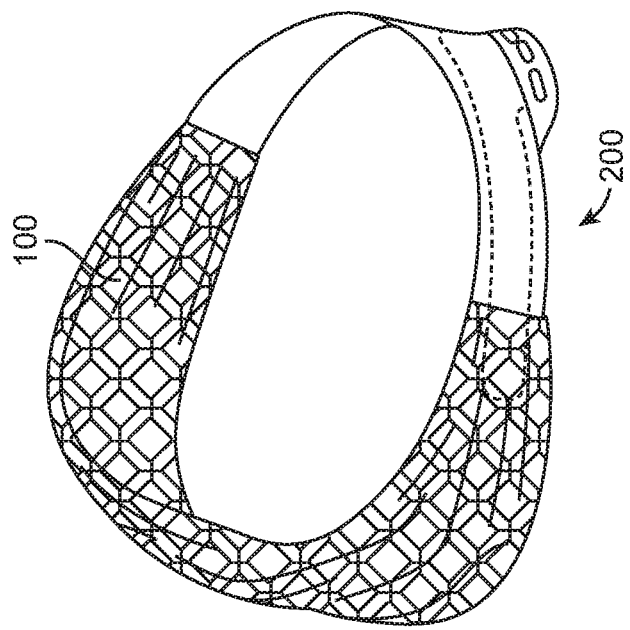
FIG. 15 is a schematic illustration of a monitoring system according to an embodiment of the present invention.
Figure 14:
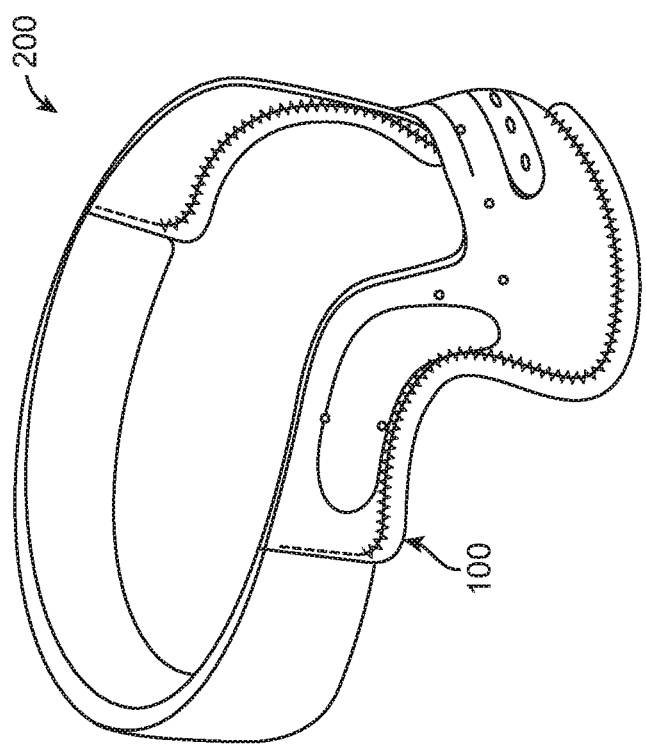
FIG. 14 is a schematic illustration of a monitoring system according to an embodiment of the present invention.
Figure 16:
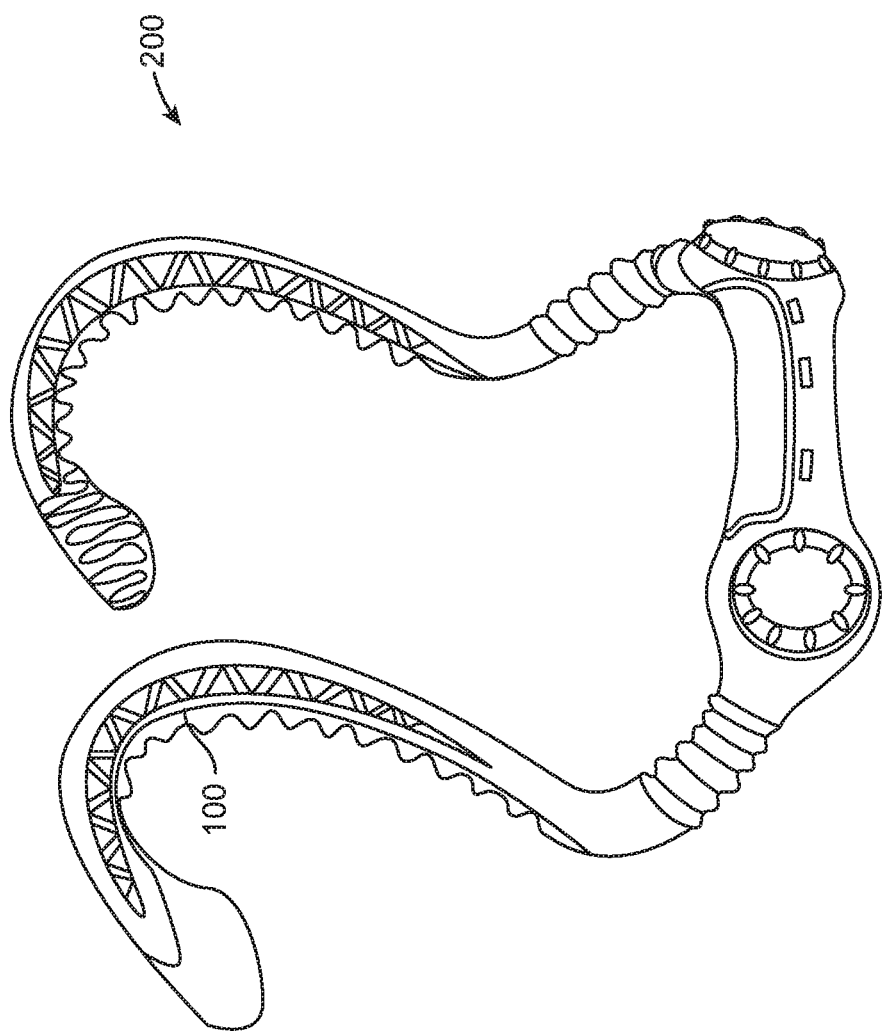
FIG. 16 is a schematic illustration of a monitoring system according to an embodiment of the present invention.
Figure 17C:
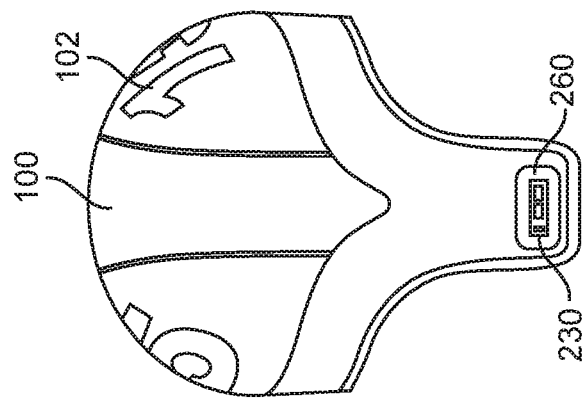
FIG. 17C is a rear view of a monitoring system for use in competition according to an embodiment of the present invention.
Figure 17B:
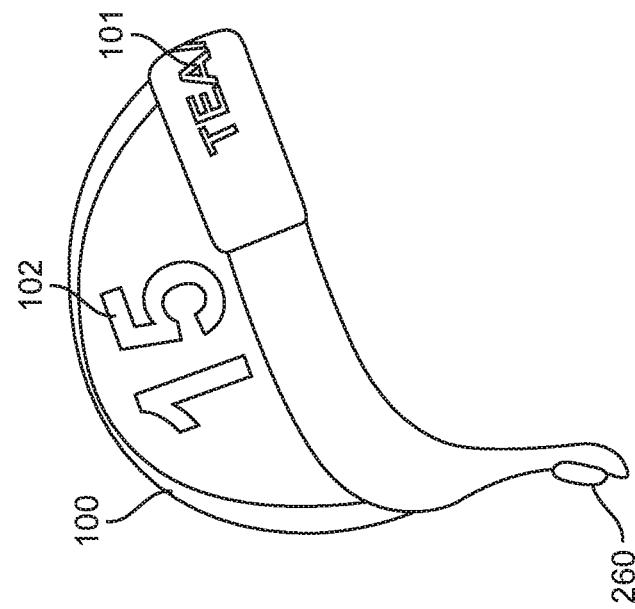
FIG. 17B is a side view of a monitoring system for use in competition according to an embodiment of the present invention.
Figure 17A:
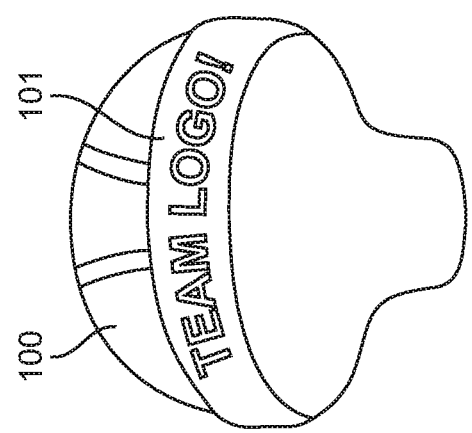
FIG. 17A is a front view of a monitoring system for use in competition according to an embodiment of the present invention.

Flexible article 100 may comprise any suitable device for mounting on the body of the user, particularly the head of the user. As discussed above, in one embodiment flexible article 100 may comprise a hat conformable to the head of the user. In another embodiment, as shown in FIG. 11, flexible article 100 may comprise a baseball style cap or visor. In another embodiment, as shown in FIGS. 12 and 13, flexible article 100 may comprise protective eyewear. The device may include protective goggles or a face mask. In another embodiment, as shown in FIG. 14, flexible article 100 may comprise an athletic headband. In another embodiment, as shown in FIG. 15, flexible article 100 may comprise a casual or fashion hair or headband. The headband may include an opening to allow the hair of the user to pass through the headband, e.g., to accommodate a ponytail. In another embodiment, as shown in FIG. 16, flexible article 100 may comprise a headset adapted to be worn around the ears of the user. In one embodiment, monitoring system 10 may be adapted for use during a competitive activity. In such an embodiment, as shown in FIGS. 17A-C, flexible article 100 may incorporate a team logo 101, team colors, a player number 102, or other graphical elements. In FIGS. 11-13, flexible article 100 is shown as comprising a Y-shaped monitoring assembly 200. In other embodiments, monitoring assembly 200 is not Y-shaped and instead may be substantially linear, for example, to fit more traditionally styled ball cap, goggle strap, and mask strap flexible articles.

In one embodiment, the monitoring assembly 200 may provide an indication to the user when a certain condition has occurred. For example, if measured data or a corresponding parameter value exceeds a threshold value, processor 220 may send a signal to display 230 and display 230 may provide a visual and/or audible indication to the user. Processor 220 may similarly send a signal to display 230 to provide an indication that a threshold value has not been exceeded. As shown in FIG. 18, for example, display 230 may include one or more light emitting diodes (LEDs). The LEDs may include different colors (e.g., green, yellow, red) to indicate the current impact severity to the user. For example, display 230 may illuminate a green LED to indicate a first impact severity (e.g., a threshold value has not been exceeded), a yellow LED to indicate a second impact severity (e.g., the data is within a predetermined range), and a red LED to indicate a third impact severity, for example, that a large head acceleration, or a large accumulation of head accelerations, has occurred (e.g., a threshold value has been exceeded). One or more LEDs may also be used to provide an indication of the operation of the monitoring system. For example, one or more LEDs may be used to indicate the power level of the system. For example, a green LED may be used to indicate that the power level of the system is adequate, while an amber LED may be used to indicate that the power level of the system is low. As shown in FIG. 19, for example, display 230 may include a liquid crystal display (LCD) having icons for indicating user or system conditions. As shown in FIG. 20, for example, display 230 may include a electrophoretic display (EPD) to illustrate a progressive level relating to user or system conditions. E-Ink Corporation of Cambridge, Mass. is one possible supplier of EPD technology. In some embodiments, as shown for example in FIG. 18, display 230 may include a speaker 232 for providing audible information or alerts to the user. The audible alert may be used in conjunction with, or instead of, a visual display. In one embodiment, display 230 may provide one or more indication patterns to indicate a current impact severity. Indication patterns may include a solidly lit LED, or a blinking or pulsing light pattern, for example. The time profile of the blinking or pulsing of the LED may provide an indication of the current impact severity. For example, an LED may rapidly blink when a threshold value is exceeded. In one embodiment, the indication that a threshold value has been reached may be indicated by a physical or tactile sensation, such as, for example, a vibration.

In one embodiment, display 230 is located on housing 260 and is sufficiently large to be visible from a distance. Display 230 may be used to provide information to the wearer of the monitoring system 10 or an individual (e.g., coach, trainer, supervisor, or parent) who is monitoring the data provided by the system. In some embodiments, display 230 may be separate from the housing 260. In one embodiment, display 230 may be a separate device. For example, display 230 may be a wristwatch-type device, and monitoring assembly 200 may communicate the user or system information to the device for viewing by the wearer or another individual. In one embodiment, display 230 is part of a remote computing device viewable by an individual monitoring the data. The monitoring assembly 200 may communicate the information to the separate display 230 via a wireless or wired connection.

Figure 21:
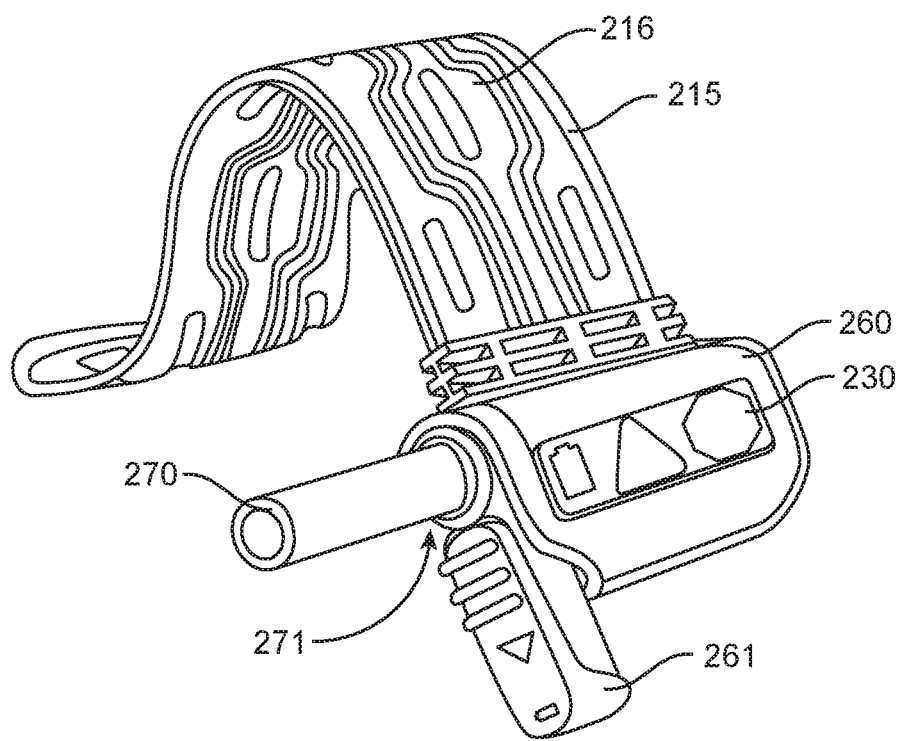
FIG. 21 is a schematic illustration of a battery powered monitoring system according to an embodiment of the present invention.

In one embodiment, as shown, for example, in FIG. 21, power source 270 may comprise a battery. The battery shown in the drawing is for illustrative purposes only. Monitoring system 10 may be adapted to be powered by any battery type or other power technology, including, but not limited to, rechargeable and non-rechargeable batteries, thin-film batteries, die-level solid state batteries, fuel cells, ultra-capacitor technologies, coin cell batteries, energy harvesting or scavenging (e.g., kinetic energy or waste heat capture), and solar power. Housing 260 may include a compartment 271 for receiving the battery and placing the battery in contact with power contacts (not shown). Housing 260 also may include a battery door 261 to facilitate access to the power source. Other suitable power sources may be used.

In one embodiment, monitoring assembly 200 may include a power management module 280 adapted to turn on/off the monitoring system 10 and to manage power consumed by the system. In one embodiment, power management module 280 includes one or more strain gauges 282 for measuring a resistance indicative of whether the system is in use, and, correspondingly whether power should be supplied to monitoring assembly 200. In one embodiment, as shown in FIGS. 22 and 23, first and second strain gauges 282 are disposed on flexible strip 215 and are operatively connected to processor 220. A stretchable band 284 including one or more resistive threads 285 connects first arm 213 and second arm 214 of flexible strip 215. In one embodiment, stretchable band 284 may connect first 213 and second 214 arms at the front of the head of the wearer. The first and second strain gauges 282 are operatively connected to opposite ends of the resistive threads 285 and are adapted to measure the resistance across the threads.

When the system 10 is not in use, as shown, for example, in FIG. 22, stretchable band 284 and, correspondingly, the resistive threads 285, are in an un-stretched position. In this position, the strain gauges 282 measure a resistance indicative that the system is not in use and do not signal the processor to turn the system on. As a result, the system 10 may be in an OFF or low-power (e.g., sleep mode) state. When a user places the monitoring system 10 including the flexible strip 215 on, the user's head stretches the band 284 and, correspondingly, the resistive threads 285, into a stretched position. In this position, as shown, for example, in FIG. 23, the strain gauges 282 measure a resistance indicative that the system is in use. The strain gauges 282, in turn, may provide a signal to processor 220 to turn on the system. As will be appreciated, the strain gauges 282 may be incorporated into other embodiments of the flexible strip 215 and monitoring assembly 200.

Figure 6A:
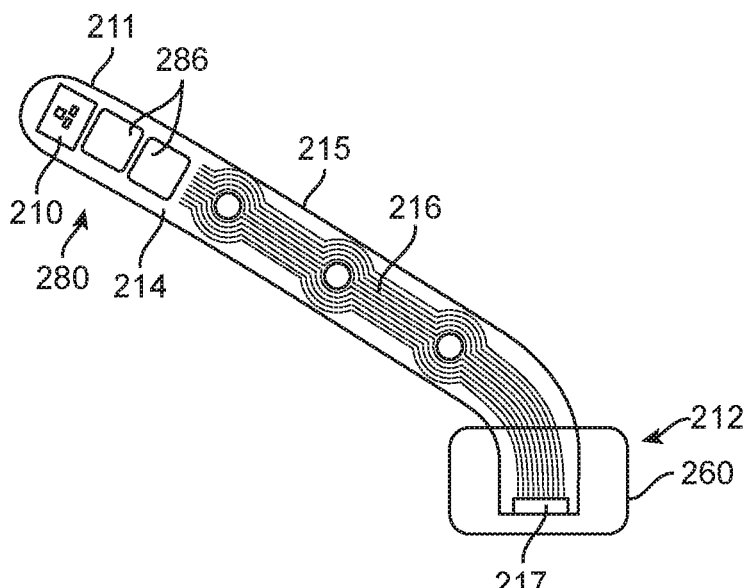
FIG. 6A is a plan view of a flexible strip including a sensor according to an embodiment of the present invention.
Figure 6B:
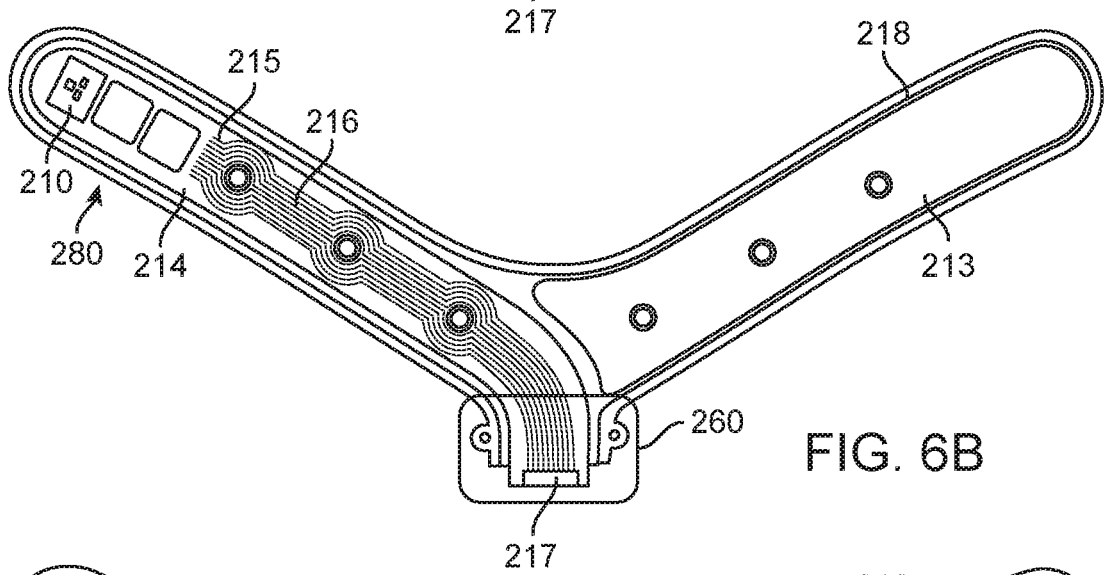
FIG. 6B is a plan view of a partially encapsulated flexible strip of FIG. 6A according to an embodiment of the present invention.
Figure 6C:
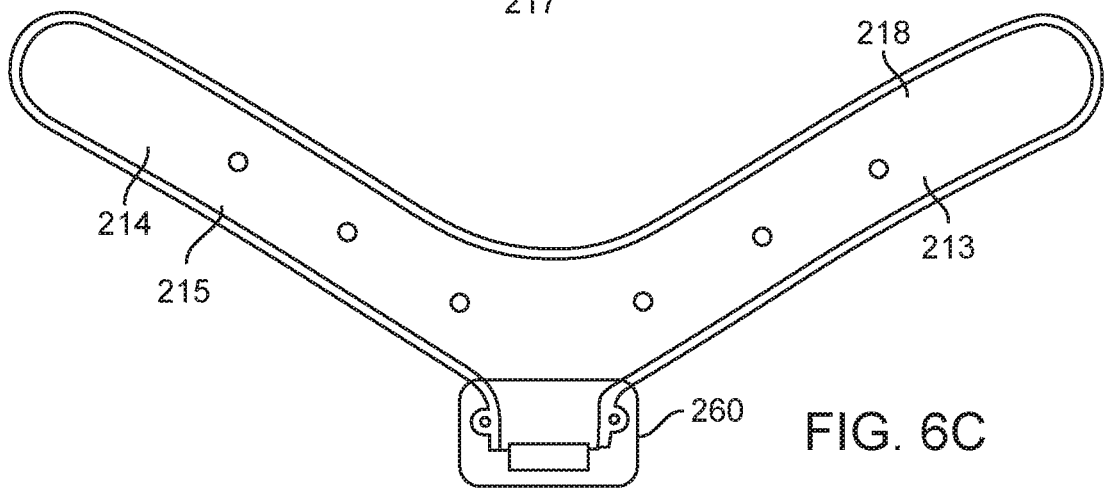
FIG. 6C is a plan view of an encapsulated flexible strip according to an embodiment of the present invention.

In one embodiment, as shown in FIG. 6A, for example, power management module 280 may include one or more proximity sensors 286 operatively connected to the flexible strip 215. Proximity sensors 286 are adapted to determine whether the sensor and, correspondingly, the flexible strip 215 are positioned proximate to the head, indicating that the system 10 is in use. Proximity sensors 286 may comprise a capacitive sensor, a photoelectric sensor, an infrared sensor, contact sensor, temperature sensor, or any other suitable sensor for determining the proximity of the system 10 to the head. In one embodiment, when it is determined that the sensor is proximate to the head, a proximity sensor 286 may send a signal to processor 220 to turn on the system. When the sensor is no longer proximate to the head, a proximity sensor 286 may send a signal to processor 220 to turn off the system or proceed to a sleep mode. In one embodiment, a first proximity sensor 286 may initiate turning on the system and a second proximity sensor 286 may initiate turning off the system. Using multiple sensors may improve reliability and efficiency of the power management in some embodiments.

Figure 25:
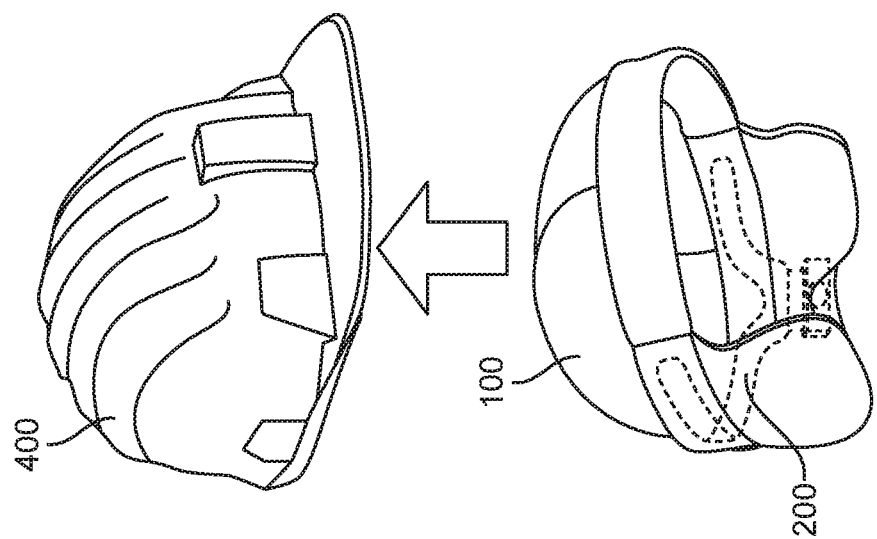
FIG. 25 is a schematic illustration of a modular monitoring system according to an embodiment of the present invention.
Figure 24:
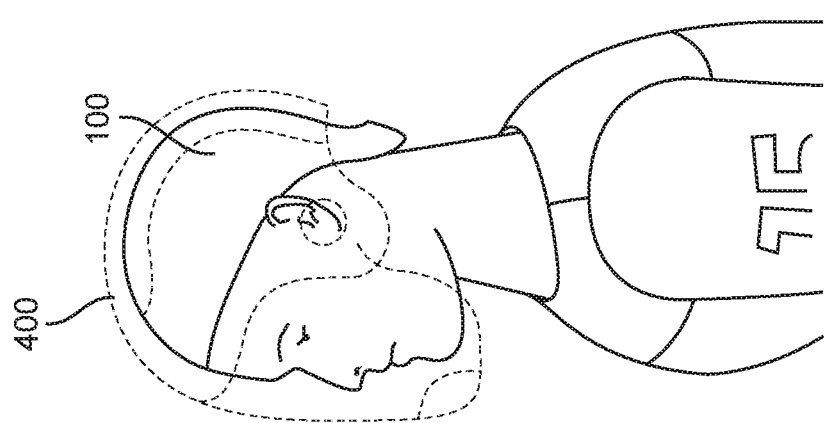
FIG. 24 is a schematic illustration of a modular monitoring system according to an embodiment of the present invention.

In one embodiment, monitoring system 10 may comprise a modular head impact monitoring system. Because the flexible article 100 is a separately wearable article of clothing of conformal construction, it may be used with virtually any other article of clothing, including other headgear, such as a rigid helmet 400. In one embodiment, the system includes a rigid helmet 400 for protecting the head of a wearer. The flexible article 100 may be adapted to be worn intermediate the rigid helmet and the head such that sensor 210 may be disposed immediately proximate to the head, or in contact with the head, for measuring an acceleration of the head. Accordingly, flexible article 100 is adapted to be worn separately from the helmet 400 and may be used interchangeably with other helmets or articles. The rigid helmet 400 may be a sports helmet, as shown in FIG. 24, for example, an industrial helmet, as shown in FIG. 25, for example, a military helmet, or virtually any headgear or article of clothing.

Figure 26B:
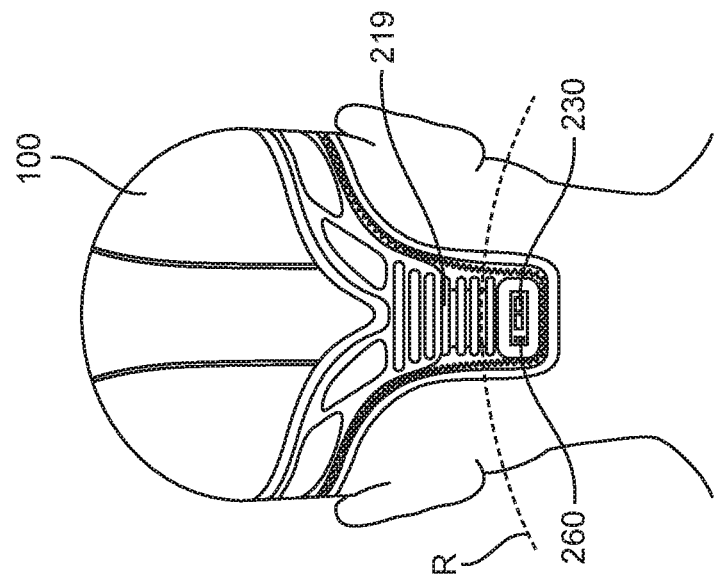
FIG. 26B is a rear view of a monitoring assembly of FIG. 26A having a flexible neck region according to an embodiment of the present invention.
Figure 26A:
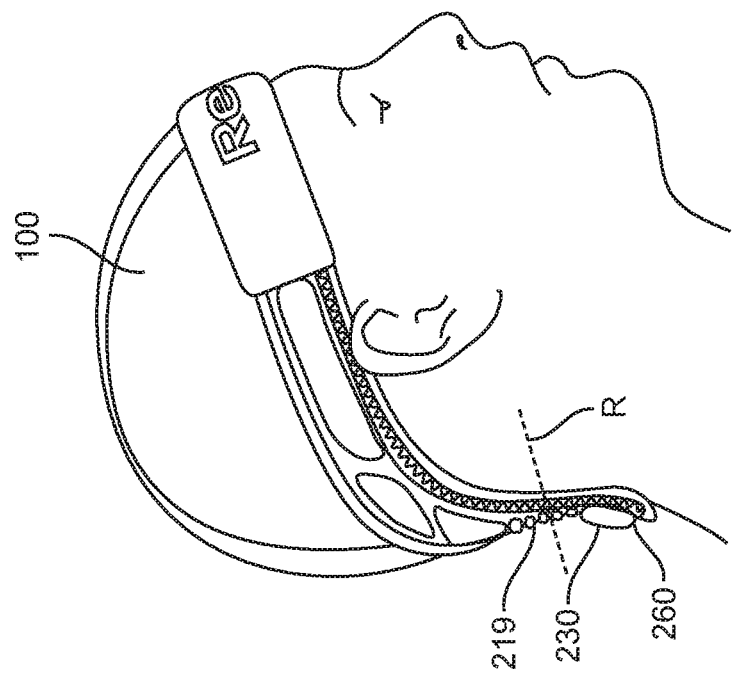
FIG. 26A is a side view of a monitoring assembly having a flexible neck region according to an embodiment of the present invention.

In one embodiment, as shown in FIGS. 26A and 26B, flexible strip 215 includes a flexible neck region 219. In one embodiment, flexible neck region 219 provides greater flexibility and/or stretchability than other portions of flexible strip 215. In some embodiments, flexible neck region 219 may be positioned at the base of the wearer's neck so as to provide improved mobility and comfort during bending and rotation of the neck and head. In embodiments in which monitoring system 10 may be used with a rigid helmet 400, flexible neck region 219 may correspond with the back radius R of the helmet. In some embodiments, flexible strip 215 may be bent at flexible neck region 219 onto the back of the helmet such that housing 260 of control unit 205 may be attached to the back of the helmet. Housing 260 may be configured such that display 230 is outwardly visible and may be attached to helmet 400 by adhesive or other suitable means.

Figure 27:
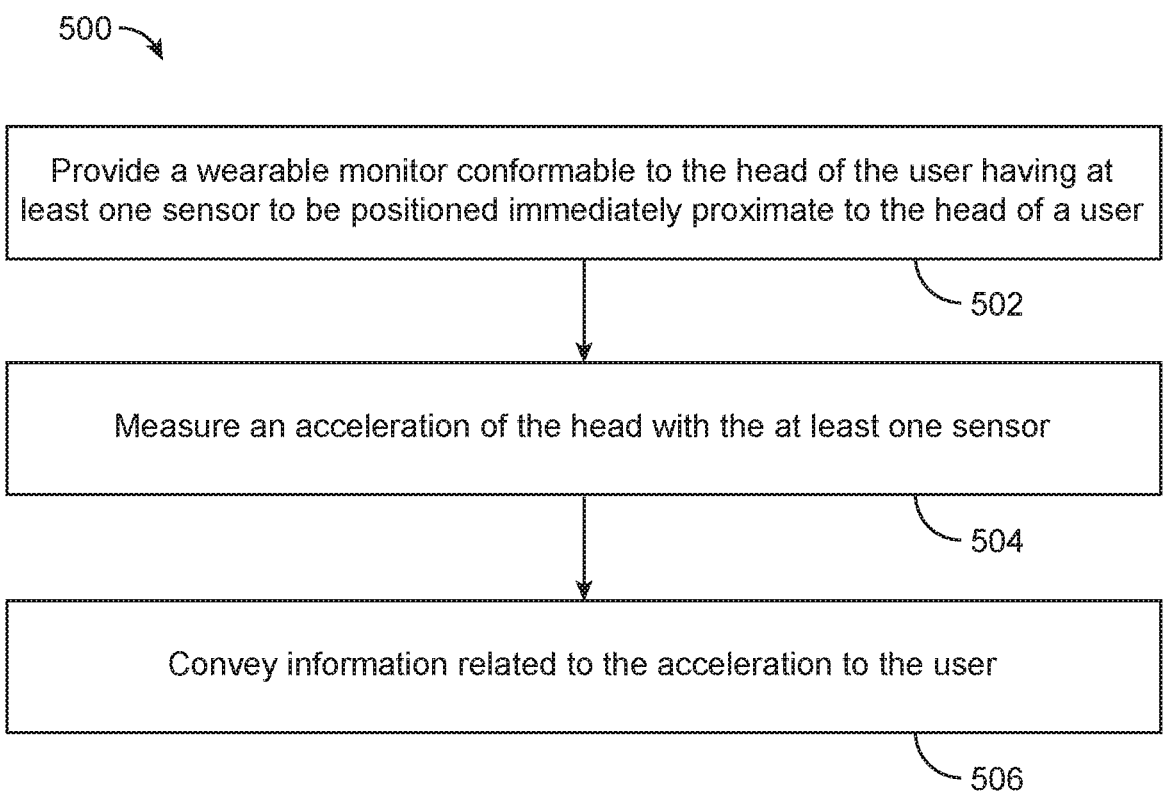
FIG. 27 is a process flowchart of a method of monitoring forces on the head of a user according to an embodiment of the present invention.

FIG. 27 is a process flowchart for a method 500 of monitoring forces on the head of a user according to an embodiment of the present invention. Method 500 may include at least steps 502, 504, and 506. Embodiments of system 10, as described herein, will be used to describe method 500, but the method is not intended to be limited thereto. Step 502 includes providing a wearable monitor 200 conformable to the head of the user having at least one sensor 210 to be positioned immediately proximate to or in contact with the head, or portion of the head (e.g., the skull, the cranium, the frontal bone, the temporal bone, the parietal bone, the sphenoid bone, the occipital bone, the scalp, or a combination thereof), of a user. In one embodiment, the monitor 200 may be removably attached to a flexible and stretchable headpiece 100, such as, for example, a hat. Step 504 includes measuring an acceleration of the head with the at least one sensor 210. Because the sensor 210 is provided immediately proximate to, or in contact with, the head, the monitor 200 may provide accurate data regarding the acceleration undergone by the head, and the force or forces acting on the head. Step 506 includes conveying information related to the acceleration to the user. The information may be displayed on a display 230, which may be mounted on or remote from the user, and may include visual, audible, and/or other information related to the acceleration data. For example, the information may include an alert that a single force or cumulative forces over time acting on the head of the user have exceeded a threshold level.

Figure 28:
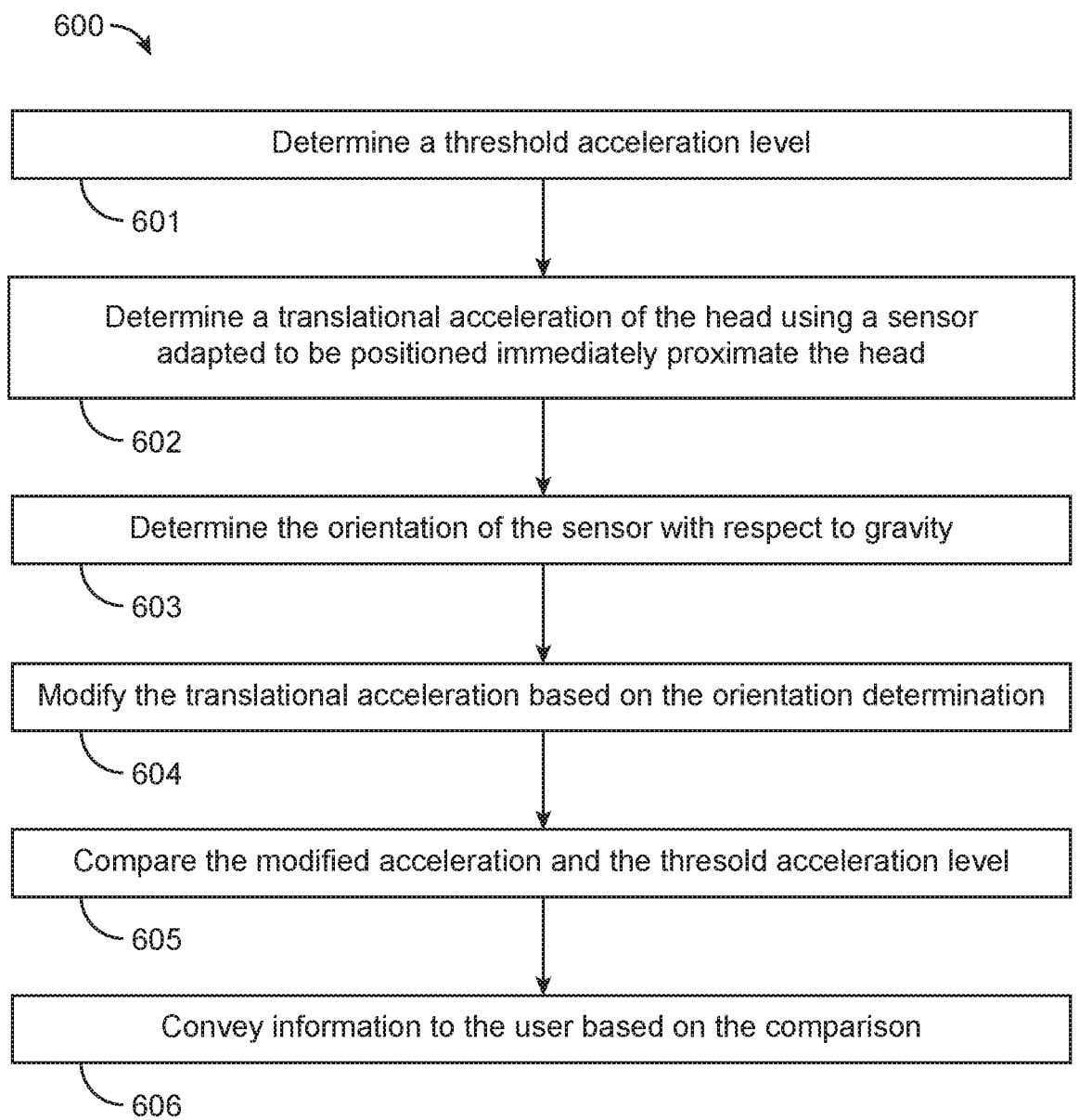
FIG. 28 is a process flowchart of a method of monitoring acceleration of the head of a user and corresponding forces acting thereon according to an embodiment of the present invention.

FIG. 28 is a process flowchart for a method 600 of monitoring acceleration of the head of a user and corresponding forces acting thereon according to an embodiment of the present invention. Method 600 may include one or more of steps 601, 602, 603, 604, 605 and 606. Embodiments of system 10, as described herein, will be used to describe method 600, but the method is not intended to be limited thereto. Step 601 includes determining a threshold acceleration level. In one embodiment, the threshold acceleration level may correlate with an acceleration thought to be non-traumatic. In one embodiment, the threshold value may be based on physiological parameters of the particular user, including, but not limited to, the user's age, height, weight, physical condition, gender, head trauma history, and other medical history data points. In one embodiment, the threshold value may be based on medical testing of the user conducted prior to use of the system 10. The threshold value may be input into the system 10, for example, via user interface 240 or a computer in communication with monitoring assembly 200 and stored in memory 250. In some embodiments, the threshold value is not user modifiable.

In step 602, the method determines a translational acceleration of the head using a sensor, such as sensor 210 comprising a low-g accelerometer, adapted to be positioned immediately proximate to or in contact with the head. In one embodiment, the sensor 210 may be removably attached to a flexible and stretchable headpiece 100, such as, for example, a hat. Translational acceleration of the head can be measured by an accelerometer, such as low-g accelerometer, or translational acceleration can be partially measured and partially estimated, with the estimation being quantitative or qualitative. Estimation of translational acceleration not measured by the accelerometer can be based upon values derived directly or indirectly from accelerometer. In some embodiments, estimation of translational acceleration not measured by the accelerometer can be made using a value derived from at least one of the following techniques: (1) determining at least one rising slope of impact acceleration; (2) determining at least one falling slope of impact acceleration; (3) determining duration of at least one estimation period; (4) determining polarity of at least one impact acceleration on one or more perpendicular measurement axes (e.g., x, y, z); (5) determining the order in which perpendicular measurement axes (e.g., x, y, z) detect translational acceleration (e.g., peak translational acceleration); (6) determining time between detected translational accelerations (e.g., peak translational accelerations) as measured on each perpendicular measurement axis (e.g., x, y, z); (7) determining the number of positive to negative acceleration transitions (e.g., zero axis crossings) on at least one perpendicular measurement axis (e.g., x, y, z); (8) determining the duration of the impact acceleration (e.g., across individual and/or all measurement axes (e.g., x, y, z), (9) integrating an impact acceleration (e.g., determining the area under the curve) for individual or for all measurement axes (e.g., x, y, z); and (10) by collecting and analyzing training or calibration data that is supplied to the system. In some embodiments, estimation of the translational acceleration not completely measured by the accelerometer may be done algorithmically or heuristically (e.g., based upon collected training or calibration data supplied to the system).

In some embodiments, the determination of translational acceleration in step 602 further comprises using additional velocity or direction information to determine translational acceleration. For example, a global positioning system (GPS) receiver or inertial sensor (e.g., an INS-type sensing device) can be used to augment data received from the accelerometer. In some embodiments, estimation of the portion of translational acceleration not measured by the accelerometer may also be based upon measurements from such other sensors.

In step 603, the method determines the orientation of the sensor with respect to gravity. The sensor may be adapted to determine the relative orientation of the sensor axes with respect to gravity. In some embodiments, processor 220 may determine the relative orientation based upon data provided to it by the sensor. The relative orientation information may be used to determine rotation of the head and may be used in determining a qualitative or quantitative measurement of the force acting on the wearer's head. In one embodiment, the sensor may include a gyroscope to measure the orientation. In step 604, the method modifies the translational acceleration based on the orientation determination. The level of acceleration experienced by the head can be greatly affected by the orientation of the head when the acceleration occurred. For example, if the head quickly rotates during or as a result of the acceleration, the effective acceleration acting on the head may be greatly increased. Accordingly, in some embodiments, it may be useful to modify a measured translational acceleration with head orientation data. The modification calculation may be conducted by processor 220 using a sensing algorithm stored thereon. Translational acceleration (e.g., measured and/or estimated) can be modified by the detected orientation in one or more of the following ways: (1) priority weighting of one or more of the perpendicular measurement axes (e.g., x, y, z); (2) increasing or decreasing measured and/or estimated translational acceleration (e.g., peak translational acceleration); (3) increasing or decreasing the duration of the impact acceleration measurement interval; and (4) increasing or decreasing the determined acceleration threshold.

In step 605, the method compares the modified acceleration value and the threshold acceleration value. In one embodiment, the processor 220 executes a comparison algorithm comparing the modified acceleration value with the user's threshold acceleration value. The modified acceleration may be a value based on a single modified acceleration measurement or may be based on a plurality of modified acceleration measurements such that the comparison takes into account the cumulative forces acting on the head of the user over time. In some embodiments, integrating the effect of multiple impacts and forces over time can be done to provide an indication that a threshold amount of energy has been delivered to the head such that, although a series of impacts may not trigger an indication individually, the accumulation of force and energy can trigger an indication. The modified acceleration value can be compared to a threshold acceleration, to a threshold acceleration selected from a set of thresholds, or to multiple prioritized threshold accelerations (e.g., via a decision tree or if-then-else logic). In the case of a set of thresholds, the selection of the threshold can be based upon orientation or can be selected based upon location and direction of impact to the head (e.g., front/back, left/right, top/bottom, etc.). The acceleration threshold(s) can be static (e.g., pre-programmed into the system) or dynamic. A dynamic acceleration threshold can be adjusted based upon head orientation, body orientation, pre-impact velocity, impact location, impact direction, cumulative direction of impacts, cumulative location of impacts, cumulative intensity of impacts, or cumulative number of impacts, or a combination thereof. Based on a comparison, the processor determines the user's current impact severity relative to the threshold value.

In step 606, the method then conveys information to the user based on the comparison. The information may be displayed on a display 230, which may be mounted on or remote from the user, and may include visual, audible, and/or other information related to the acceleration data. For example, display 230 may illuminate a green LED to indicate a first impact severity (e.g., the threshold value has not been exceeded), a yellow LED to indicate a second impact severity (e.g., the data is within a predetermined range), and a red LED to indicate a third condition, for example, that a large head acceleration, or a large accumulation of head accelerations, has occurred (e.g., a threshold value has been exceeded).

In some embodiments, method 600 can also include the step of determining at least one of a location of an impact to the head or a direction of an impact to the head. In addition, method 600 can also include the step of selecting the predetermined threshold acceleration level based upon at least one of the location of the impact and the direction of the impact.

In embodiments using a low-g accelerometer, processor 220 may be adapted to extrapolate any received data that may occur outside of the range of the accelerometer. For example, if sensor 210 determines that an acceleration of the head has occurred outside the sensor's measurable range, sensor 210 may send a signal to processor 220 indicating that a high range of acceleration has occurred. Processor 220 may be adapted to estimate the level of the high range acceleration that occurred. Translational acceleration of the head can be measured by sensor 210 (e.g., a low-g accelerometer), or translational acceleration can be partially measured and partially estimated, with the estimation being quantitative or qualitative. Estimation of translational acceleration not measured by the sensor 210 can be based upon values derived directly or indirectly from the sensor. In some embodiments, estimation of translational acceleration not measured by the sensor can be made using a value derived from at least one of the techniques detailed supra with regard to step 602 of FIG. 28.

In other embodiments, the system 10 may include other reference data during monitoring. For example, reference data indicative of brain activity may be used. For example, in one embodiment, prior to using the system 10, a user may undergo testing to define a baseline for their impact tolerance. In other embodiments, reference data may include a value that correlates with an acceptable impact severity for an individual with a similar profile as the user (e.g., age, size, etc.).

In some embodiments, monitoring assembly 200 may include other sensors adapted to measure qualitative and quantitative parameters relating to the user and/or the environment, including, but not limited to, sensors for measuring temperature, humidity, respiration, hydration, blood pressure, acoustics, brain activity, electrical activity of muscles, heart rate, pulse, and pressure. For example, monitoring assembly 200 may comprise at least one additional sensor selected from the group consisting of temperature sensors, respiration sensors, hydration sensors, blood pressure sensors, sensors to measure electrical activity of the heart or other muscles (e.g., via ECG, EMG, or EKG), and heart rate sensors. In some embodiments, data collected from such additional sensors could be used to modify a threshold level for impact severity. For example, a user's tolerance for impact may differ under conditions of elevated temperature, dehydration, and/or elevated heart rate and monitoring assembly 200 could modify the threshold level for impact severity based upon such additional data. In other embodiments, these additional sensors could be used to collect various data and convey trends in such data to the user. In some instances, data collected from such sensors can be compared to threshold values and information concerning a comparison of the measured data to the threshold can be conveyed to the user.

Figure 29:
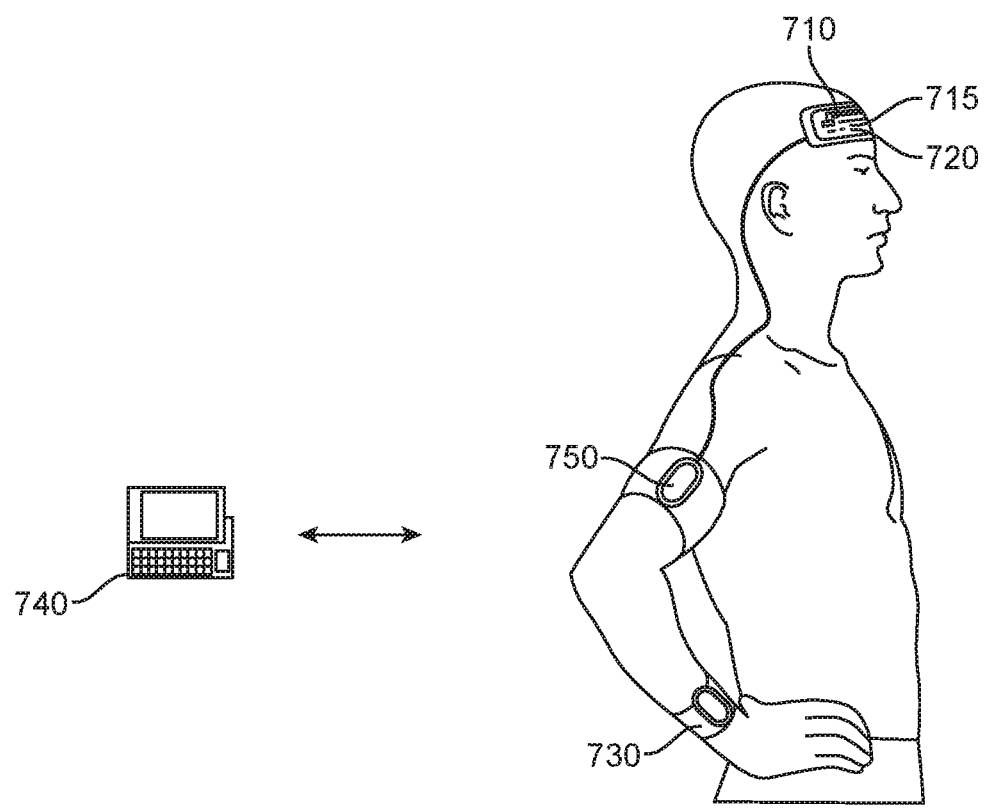
FIG. 29 is a schematic illustration of a monitoring system according to an embodiment of the present invention.

In one embodiment, as shown, for example, in FIG. 29, a flexible strip 715 may comprise a patch adapted to be secured directly to the head or body of the user. Flexible strip 715 may include adhesive or other suitable means for securing the patch to the user, for example, at the forehead, the temple area, or rear area of the head. In some preferred embodiments, at least one flexible strip 715 patch is secured to the user's skin in the vicinity of the skull, the cranium, the frontal bone, the temporal bone, the parietal bone, the sphenoid bone, and/or the occipital bone. In specific embodiments, at least one flexible strip 715 patch is secured to the user's skin in the vicinity of the temporal bone or the parietal bone. Flexible strip 715 may comprise a thin layer of flexible, conductive material having all of the necessary components of monitoring assembly 200 disposed thereon, including one or more sensors 710 and processor 720, and may be in communication (e.g., wired or wireless communication) with a display 730 remote from the flexible strip 715. The display 730 may include a wristwatch type device 730 worn by the user, a remote computer 740, or other display means. One or more other body sensors 750 may also be in communication (e.g., wired or wireless communication) with flexible strip 715. The flexibility and thin construction of flexible strip 715 facilitates placement of the sensor 720 immediately proximate to or in contact with the head of the wearer.

Figure 30:
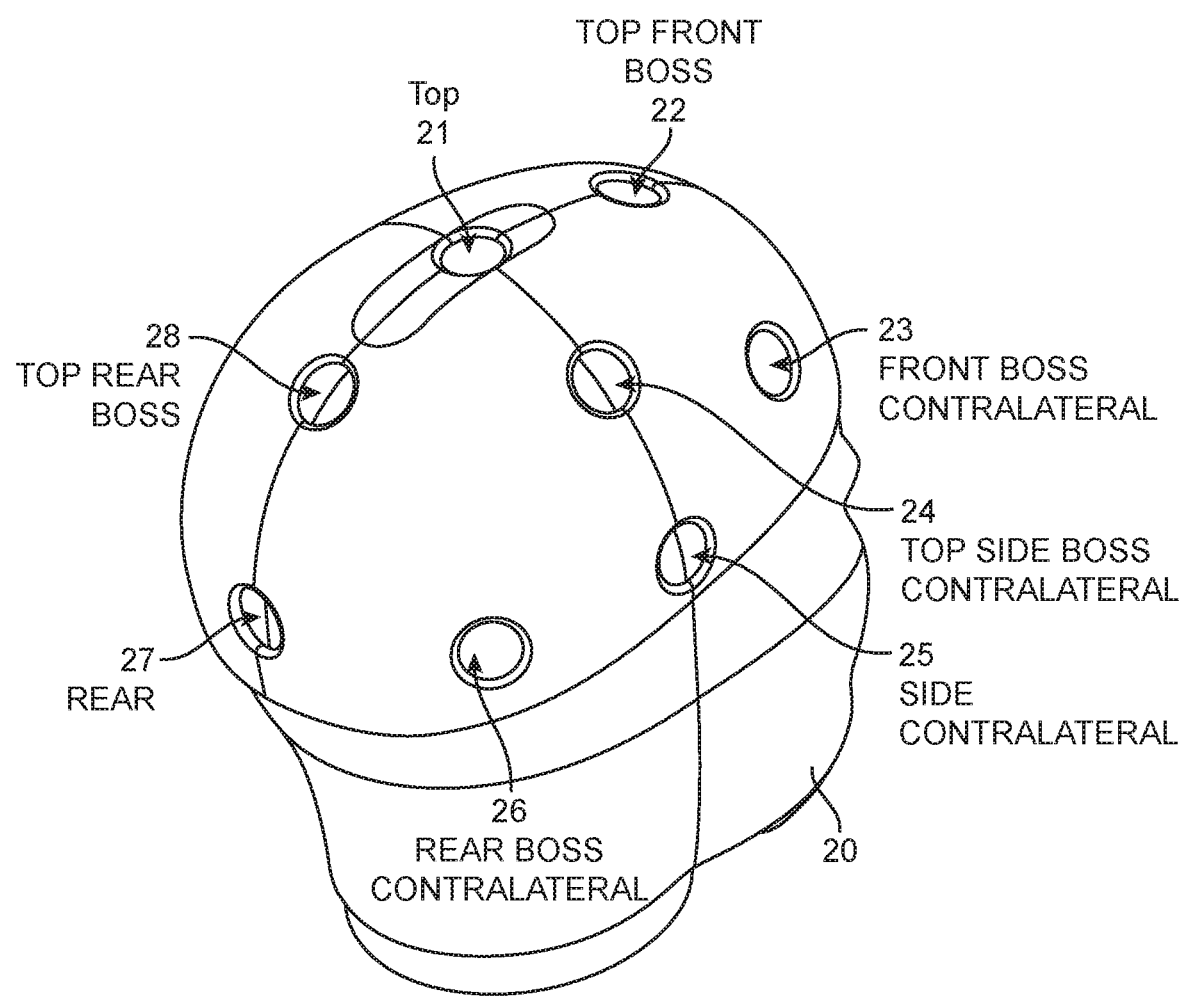
FIG. 30 is a schematic illustration of head regions of a monitoring system according to an embodiment of the present invention.
Figure 31:
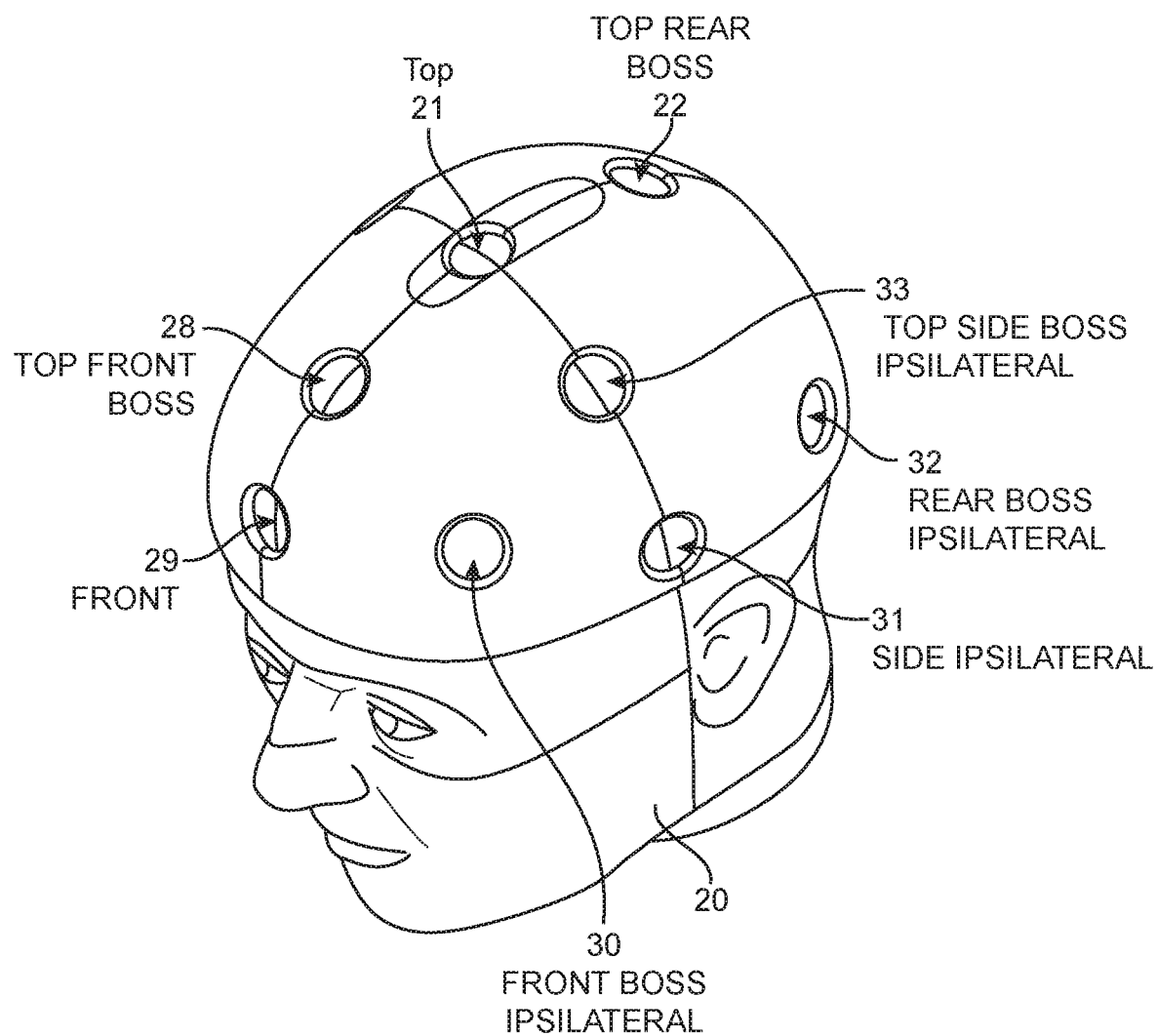
FIG. 31 is a schematic illustration of head regions of a monitoring system according to an embodiment of the present invention.

In some embodiments, monitoring assembly 200 is adapted to determine the location of an impact on the head. The data provided by a sensor of the monitoring assembly 200 may indicate one or more regions of the head which have received an impact. For example, with reference to FIGS. 30 and 31, head regions may include top region 21, a top front boss region 22, a front boss contralateral region 23, a top side boss contralateral region 24, a side contralateral region 25, a rear boss contralateral region 26, a rear region 27, a top rear boss region 28, a front region 29, a front boss ipsilateral region 30, a side ipsilateral region 31, a rear boss ipsilateral region 32, and a top side boss ipsilateral region 33. The number and location of the various head regions is intended to be illustrative. In other embodiments, additional (or fewer) regions may be used and may be defined by different locations on the head. By determining a particular region(s) of the head that received an impact, the monitoring assembly 200 may provide an accurate assessment of the head condition.

In one embodiment, during operation a sensor of the monitoring assembly 200 may be coupled externally to the side of the head (e.g., above the left ear) to measure the sustained impact or acceleration to the device. The values from the monitoring assembly 200 may be matched to an acceleration reading that is measured at the internal center of mass of a headform 20 during simulated impacts. Each impact and subsequent impact region (e.g. front, top front boss) is a different distance away from the center of mass of the head (brain) and is also a different distance away from a sensor of the monitoring assembly 200 (e.g., externally above the left ear/side ipsilateral). Therefore, the relationship between the measurement from the monitoring assembly 200 and the measure at the center of mass of the head will change depending upon the impact location/zone. The impact locations/zones are used to account for or adjust for this difference.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A device for monitoring a force acting on a head of a user, comprising:
    a flexible article configured to be worn on the head of the user; and
    a monitoring assembly removably coupled to the flexible article, the monitoring assembly including:
        a sensor for measuring a force on the head and transmitting data relating to the force, the sensor positioned to be disposed immediately proximate to the head;
        a processor configured to receive the force data from the sensor; and
        a flexible strip operatively connecting the sensor and the processor, the flexible strip including a first end and a second end,
    wherein the sensor is disposed at the first end of the flexible strip and the control unit processor is disposed intermediate to the first end of the flexible strip and the second end of the flexible strip,
    wherein a neck portion of the flexible strip extends downwardly and is configured to be positioned at a base of a neck of the user, and
    wherein the processor is coupled to the neck portion.

2. The device of claim 1, further comprising a pocket formed in the flexible article, and wherein at least a portion of the monitoring assembly is disposed in the pocket.

3. The device of claim 1, wherein at least a portion of the monitoring assembly is securely attached to the flexible article.

4. The device of claim 1, wherein the sensor comprises an accelerometer configured to measure an acceleration of the head.

5. The device of claim 1, wherein the sensor comprises a plurality of accelerometers.

6. The device of claim 1, wherein the sensor further comprises at least one gyroscope.

7. The device of claim 1, wherein at least a portion of the monitoring assembly is disposed between an outer flexible layer and an inner flexible layer of the flexible article.

8. The device of claim 1, wherein the flexible article is configured to conform to a crown of the head of the user.

9. The device of claim 1, wherein the flexible article is configured to conform to at least one portion of the user's head proximate to a region selected from the group consisting of the cranium, the frontal bone, the temporal bone, the parietal bone, the sphenoid bone, the occipital bone, the scalp, and combinations thereof.

10. The device of claim 1, wherein the sensor positioned to be disposed immediately proximate to the head is positioned to be disposed proximate to the temporal bone or the parietal bone of the head.

11. The device of claim 1, wherein the sensor positioned to be disposed immediately proximate to the head is positioned to be disposed proximate to the cranium.

12. A modular head impact monitoring system, comprising:
    a rigid helmet for protecting a head of a user;
    a conformal headpiece including an outermost conformal layer formable to the head of the user, the conformal headpiece configured to be worn in between the rigid helmet and the head with a portion of the conformal headpiece extending below the rigid helmet and configured to be positioned at a base of a neck of the user;
    a sensor unit for measuring an acceleration of the head, the sensor unit coupled to the headpiece and configured to be disposed in between the head and the outermost conformal layer; and
    a control unit having a processor, the control unit coupled to the portion of the conformal headpiece extending below the rigid helmet,
    wherein the sensor unit is operatively connected to the control unit, and
    wherein the conformal headpiece is configured to be worn separately from the rigid helmet.

13. The system of claim 12, wherein the rigid helmet is a sports helmet.

14. The system of claim 12, wherein the rigid helmet is an industrial helmet.

15. The system of claim 12, wherein the rigid helmet is a military helmet.

16. The system of claim 12, wherein the sensor unit is removably coupled to the conformal headpiece.

17. The system of claim 12, wherein the sensor unit comprises a flexible strip having an accelerometer disposed thereon and a contact for connecting to a processor.

18. The system of claim 17, wherein the processor is connected to the sensor unit and configured to receive acceleration data from the accelerometer.

19. A device for monitoring a force acting on a head of a user, comprising:

a flexible article configured to be worn on the head of the user, the flexible article having a pocket; and a monitoring assembly removably disposed within the pocket of the flexible article, the monitoring assembly including:

a sensor for measuring a force on the head and transmitting data relating to the force, the sensor positioned to be disposed immediately proximate to the head and proximate to the cranium and comprising at least one low-g accelerometer configured to measure accelerations of no more than 24 g;

a processor configured to receive the force data from the sensor; and a flexible strip operatively electrically connecting the sensor to the processor, wherein a neck portion of the flexible strip extends downwardly and is configured to be positioned at a base of a neck of the user, and wherein the processor is coupled to the neck portion.

20. The device of claim 19, wherein the sensor positioned to be disposed proximate to the cranium is positioned to be disposed proximate to the temporal bone or the parietal bone of the head.

* * * * *